United States Patent
Ma et al.

(10) Patent No.: US 10,071,989 B2
(45) Date of Patent: Sep. 11, 2018

(54) SUBSTITUTED CINNAMAMIDE DERIVATIVE, PREPARATION METHOD AND USE THEREOF

(75) Inventors: Xiaohui Ma, Tianjin (CN); Yuanpeng Jin, Tianjin (CN); Min Han, Tianjin (CN); Shuiping Zhou, Tianjin (CN); Wangyi Zhou, Tianjin (CN); Xuejun Luo, Tianjin (CN); Guocheng Wang, Tianjin (CN); Lulu Yan, Tianjin (CN); Lanlan Zhang, Tianjin (CN); Yonghong Zhu, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 0 days.

(21) Appl. No.: 14/128,572

(22) PCT Filed: Jun. 26, 2012

(86) PCT No.: PCT/CN2012/077549
§ 371 (c)(1),
(2), (4) Date: Dec. 20, 2013

(87) PCT Pub. No.: WO2013/000399
PCT Pub. Date: Jan. 3, 2013

(65) Prior Publication Data
US 2014/0121242 A1  May 1, 2014

(30) Foreign Application Priority Data

Jun. 27, 2011 (CN) .......................... 2011 1 0174376
Apr. 25, 2012 (CN) .......................... 2012 1 0123842

(51) Int. Cl.
| | | |
|---|---|---|
| A01N 43/40 | (2006.01) |
| A61K 31/445 | (2006.01) |
| C07D 405/06 | (2006.01) |
| C07D 317/60 | (2006.01) |
| C07D 317/62 | (2006.01) |
| C07D 317/64 | (2006.01) |
| C07D 317/50 | (2006.01) |
| C07D 317/52 | (2006.01) |

(52) U.S. Cl.
CPC ......... *C07D 405/06* (2013.01); *C07D 317/50* (2013.01); *C07D 317/52* (2013.01); *C07D 317/60* (2013.01); *C07D 317/62* (2013.01); *C07D 317/64* (2013.01)

(58) Field of Classification Search
USPC ....................................................... 514/321
See application file for complete search history.

(56) References Cited

U.S. PATENT DOCUMENTS

| | | |
|---|---|---|
| 2004/0053994 A1 | 3/2004 | Pan et al. |
| 2009/0143397 A1 | 6/2009 | Kuo et al. |

FOREIGN PATENT DOCUMENTS

| | | |
|---|---|---|
| AU | 2005201481 | 5/2005 |
| CN | 1532182 | 9/2004 |
| CN | 102240281 | 11/2011 |
| CN | 102850317 A | 1/2013 |
| EP | 0145361 | 6/1985 |
| JP | 201106888 | 4/2011 |
| KR | 100675619 | 1/2007 |
| WO | WO 02/14273 | 2/2002 |
| WO | WO 2004/033427 | 4/2004 |
| WO | WO 2005/016883 | 2/2005 |
| WO | WO2008028314 | 3/2008 |
| WO | 2011/140987 | 11/2011 |

OTHER PUBLICATIONS

Mbaze et. al. (Phytochemistry (2009) 70:1442-1447).*
Wang et. al. (Organic Letters (2010) 12:5430-5433).*
Abstract from STN: accession No. 2010:1364767 (2010).*
Linke et. al. (Tetrahedron (1978) 34:1979-1983).*
Salway (Journal of the Chemical Society, Transactions (1909) 95:1155-1165).*
Ito et. al. (Cancer Science (2003) 94:3-8).*
Dallacker et. al. (Chem. Ber. (1975) 108:95-108).*
Ito et. al. (Cancer Sci. (2003) 94:3-8).*
Bastin et. al. (Organic Process Research and Development (2000) 4:427-435).*
Office Action corresponding to co-pending New Zealand Patent Application Serial No. 618801, New Zealand Patent Office, dated Jun. 8, 2015; (2 pages).

(Continued)

*Primary Examiner* — Marcos L Sznaidman
(74) *Attorney, Agent, or Firm* — Nixon Peabody LLP

(57) ABSTRACT

The present invention relates to substituted cinnamamide derivatives, the method for preparing thereof and the use thereof. Each of said derivatives has a structure of formula (I). The method for preparing the substituted cinnamamides and their derivatives of the present invention is also disclosed. Substituted piperonal derivatives are selected as starting materials to prepare the substituted cinnamamide derivatives of the present invention by Wittig reaction and acid-amine condensation reaction. Further, a use of the present compounds in preventing and treating depressive-type mental diseases is disclosed.

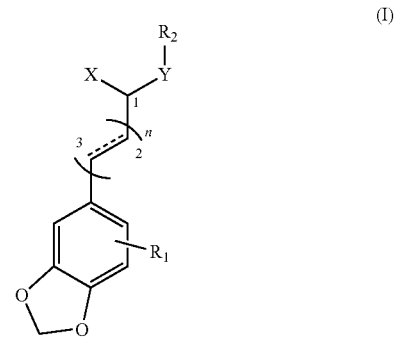

(I)

10 Claims, No Drawings

(56) References Cited

OTHER PUBLICATIONS

Office Action corresponding to co-pending Moscow Patent Application Serial No. 2014102302/04(003455), Moscow Patent Office, dated Jun. 25, 2015; (9 pages).
Liu Hongyu et al; "Studies on Chemical Constituents of Piper Austrosinense"; Natural Product Research and Development vol. 7 No. 2; (pp. 20-23)(Apr. 20, 1994).
Fatima Chaaib et al.; "Antifungal and Antioxidant Compounds from the Root Bark of Fagara zanthoxyloides"; Planta Med (pp. 316-320) (2003).
S. Linke et al.; "Wisanin Und Andere Amide Der 5-(2-Methoxy-4,5-Methylendioxyphenyl)-24,4-Pentadiensäure"; Tetrahedron vol. 34 (pp. 1979-1993) (1978).
Database Reaxys; XP-002733892; Database accession No. 40432 (RID); CAS Registry No. 855164-88-4; Journal of the Indian Chemical Society vol. 13 (pp. 260,262) (1936).
Database CA, Database accession No. 1909:15983, XP-002737937; CAS-RN 871898 (1909).
Database CA, Database accession No. 1975:563781, XP-002737938; CAS-RN 54976-69-1 (1975).
John R. Lewis; "Amaryllidaceae, Sceletium, imidazole, oxazole, thiazole, peptide and miscellaneous alkaloids"; Nat. Prod. Rep. 19, (pp. 223-258) (2002).
N S Narasimhan et al.; "Organo-Lithiation and halogen metal exchange reactions in organic synthesis—an anomolous aromatic substitution via halogen-metal exchange"; Proc. Indian Acad. Sci. (Chem. Sci.), vol. 100, Nos. 2 & 3 (pp. 205-215) (Apr. 1988).
Fen Wang et al.; "Rh(III)-Catalyzed Tandem Oxidative Olefination—Michael Reactions between Aryl Carboxamides and Alkenes"; Organic Letters 2010 vol. 12, No. 23 (pp. 5430-5433); American Chemical Society (2010).
Database Reaxys, Database accession Nos. 28220, 84598 (RIDs) & Acta Polytechnica Scandinavia, Chemistry including metallurgy series 1965, 41, pp. 1, 11-27.
Database Reaxys, Database accession No. 36327 (RID), Proceeding—Indian Academy of Scinces, Section A 1944, pp. 169-172.
Database Reaxys, Database accession No. 40432 (RID), J, Indian Chem. Soc. 1936, 13:260-262.
Database Reaxys, Database accession No. 40860, 44496 (RID), Agra University Journal of Research, Science 1954, 3:135.
Database Reaxys, Database accession No. 152107 (RID), J. Org. Chem. 1952, 19:1029-1031.
Database Reaxys, Database accession Nos. 200222, 175738 (RIDs), Itsuu Kenkyusho Nempo 1951, p. 15.
Database Reaxys, Database accession No. 6999334 (RID), Farmaco Edizione Scientifica 1985, 40:875-884.
Database Reaxys, Database accession No. 8661251 (Rx-D), Tetrahedron Lett. 2000, 41:6531-6535.
Database Reaxys, Database accession No. 13906765 (RID), Tetrahedron 2009, 65:8354-8361.
Database CA, Database accession No. 1909:15983, CAS-RN 871898.
Database CA, Database accession No. 1975:563781, CAS-RN 54976-69-1.
Alam et al., "Multi-functionalization of gallic acid towards improved synthesis of x- and beta-DDB", Tetrahedron 61:1909-1918 (2005).
Asakawa et al., "Bibenzyl derivatives from *Frullania* species", Phytochemistry 26(4):117-1122 (1987).
Continguiba et al., "Piperamides and their derivatives as potential anti-trypanosomal agents", Med Chem. Res. 18:703-711 (2009).
Correa et al., "In Vitro TRPV1 activity of piperine derived amides", Bioorg. Med. Chen. 18:3299-3306 (2010).
Dallacker et al., "Derivate des methylendioxybenzols, 6. Mitt. Uber die gewinnung und electrophile substitutionen des myristicinsauremethylesters und seiner derivate", Monatshefte Chemie 91:1089-1102 (1960).
Dallacker et al., "Derivate des methylendioxybenzols, Zur darstellung von methy-1 [3.4-methylendioxy-phenyl)-alkyl]-aminen" Chem. Ber. 104:2517-2525 (1971).
Depaula et al., "Synthesis and inspecticidal activity of new amide deivatives of piperine", Pest. Manag Sci 56:168-174 (2000).
Dominguez et al., "Short Report: Two amides from piper amalago", Phytochemistry 25(1):239-240 (1986).
Han et al., "Synthesis and structure-activity relationship of novel cinnamamide derivatives as antidepressant agents", Bioorganic & Medical Chemistry Letter 24:5284-5287 (2014).
Hudlicky et al., "Toluene dioxygenase-mediated cis-dihydroxylation of aromatics in enantioselective synthesis. Asymmetric total syntheses of pancratistatin and 7-deoxypancratistatin, promising antitumor agents", J. Am. Chem. Soc. 118:10752-10765 (1996).
Lee et al., "Piperine forms the fruits of piper longum with inhibitory effect on monoamine oxidase and antidepressant-like activity", Chem. Pharm. Bull, 53(7):832-835 (2005).
Lee et al., "Methylpiperate derivatives from piper longum and their inhibition of monoamine oxidase", Arch. Pharm. Res. 31(6):679-683 (2008).
Linke et al., "Synthesen, spektroskopische untersuchungen und prufung auf antibakterielle wirksamkeit von einigen pfeffer-alkaloiden. Olefinierungsreaktionen mit phosphorylacetamiden", Liebigs Ann. Chem. pp. 1142-1149 (1982).
Lloyd et al., "Intramolecular hydrogen bonding in ortho-substituted benzoic acids", J. Am. Chem. Soc. 88:5544-5549 (1966).
Matsuda et al., "Hepatoprotective amide constituents from the fruit of piper chaba: structural requirements, mode of action, and new amides", Bioorg. Med. Chem. 17:7313-7323 (2009).
Prashanth et al., "Synthesis, characterization, antidepressant and antioxidant activity of novel piperamides bearing piperidine and piperazine analogues", Bioorganics and Medicial Chemistry Letters, 22:7065-7070 (2012).
Rugheimer et al., Ritter Chem. Ber. 45:1340-1343 (1912).
Wei et al., "New amide alkaloids from the roots of piper migrum", J. Nat. Prod. 67:1005-1009 (2004).
Zhang et al., Synthesis and anti-proliferative in-vitro activity of two natural dihydrostilbenes and their analagoues Arch. Pharm. Chem. Life Sci. 340:244-250 (2007).
Zhihui et al., "Amides from as arum chingchengense", Phytochemistry 30(11):3797-3798 (1991).
Linke et al., "Wisanin und andere amide der 5-(2-methoxy-4,5-methylendioxyphenyl)-2,4-pentadiensaure", Tetrahedron 34:1979-1983 (1978).
Wang et al., "Molecular shape analysis and quatitative structure-anticonvulsant activity relationships of cinnamamides", Chines Journal of Chemistry 8(3):217-220 (1988).
Carlton et al., "Discovery of small molecule agonist for the bombesin receptor subtype 3 (BR-3) based on an omeprazole lead", Bioorganic & Medicinal Chemistry Letter, 18(20):5451-5455 (2008).
Niu et al., "The quatum study on structyre-activity relationship of 3, 4-methynyl-dioxy cassia-acylamide", Computers and Applied Chemistry 21(4):587-590 (2004).
Delaney e al., "Partition coefficient of some N-alkyl and N,N-dialkyl-derivatives of some cinnamamides and benzalcyanocetamides in the system cyclohexane-water", Canadian Journal of Chemistry 47:3273-3277 (1969).
Zhang et al., Journal of Peking University, 13:83-91 (1980).
Wang et al., Journal of Peking University, 14:65-70 (1982).
Li et al., Journal of Peking University, 12:153-157 (1980).
Chemical Library; Supplier: Enamine; CAS RN 878126-55-7; Mar. 27, 2006.
Chemical Library; Supplier; Aurora Fine Chemicals; CAS RN 923149-22-8; Feb. 26, 2007.
Chemical Library; Supplier: Aurora Fine Chemicals; CAS RN 923686-10-6; Feb. 28, 2007.
Chemical Library; Supplier: Enamine; CAS RN 930524-41-7; Apr. 17, 2007.
Chemical Library; Supplier: Enamine; CAS RN 930892-41-4; Apr. 19, 2007.
Chemical Library; Supplier: Enamine; CAS RN 931044-33-6; Apr. 19, 2007.
Chemical Library; Supplier: Ambinter; CAS RN 1016079-34-7; Apr. 21, 2008.
Chemical Library; Supplier: Ukrorgsynthesis; CAS RN 1050531-27-5; Sep. 19, 2008.
Chemical Library; Supplier: Ukrorgsynthesis; CAS RN 1050648-40-2; Sep. 19, 2008.

(56) References Cited

OTHER PUBLICATIONS

Chemical Library; Supplier: Ukrorgsynthesis; CAS RN 1098355-85-1; Feb. 1, 2009.
Chemical Library; Supplier: Ukrorgsynthesis; CAS RN 1099745-50-2; Feb. 2, 2009.
Chemical Library; Supplier: Ukrorgsynthesis; CAS RN 1099784-94-7; Feb. 2, 2009.
Chemical Library; Supplier: Ukrorgsynthesis; CAS RN 1099283-55-2; Feb. 2, 2009.
Chemical Library; Supplier: Ukrorgsynthesis; CAS RN 1099294-40-2; Feb. 2, 2009.
Chemical Library; Supplier: Ukrorgsynthesis; CAS RN 1099711-62-2; Feb. 2, 2009.
Chemical Catalog; Supplier: Ukrorgsynthesis; CAS RN 1152538-92-5; Jun. 5, 2009.
Chemical Catalog; Supplier: Ukrorgsynthesis; CAS RN 1152544-85-8; Jun. 5, 2009.
Chemical Library; Supplier: Ukrorgsynthesis; CAS RN 1240638-55-4; Sep. 13, 2010.
Chemical Library; Supplier: Aurora Fine Chemicals; CAS RN 1286960-13-1; Apr. 28, 2011.
Chemical Library; Supplier: Aurora Fine Chemicals; CAS RN 1287421-56-0; Apr. 29, 2011.
OA1 from corresponding JP Application No. 2014-517419 dated Feb. 24, 2015.
Dallacker et al., "Über Polyencarbonsaureimide des Methylendioxybenzols", Chemische Berichte 108:95-108 (1975) [English Abstract].
SciFinder: CAS Registry No. 1306998-73-1; STN Entry Date Jun. 7, 2011.
SciFinder: CAS Registry No. 1302585-41-6; STN Entry Date May 30, 2011.
SciFinder: CAS Registry No. 1153255-22-1; STN Entry Date Jun. 7, 2009.
SciFinder: CAS Registry No. 1099711-51-9; STN Entry Date Feb. 2, 2009.
SciFinder: CAS Registry No. 1099294-53-7; STN Entry Date Feb. 2, 2009.
SciFinder: CAS Registry No. 930860-43-8; STN Entry Date Apr. 19, 2007.
SciFinder: CAS Registry No. 878264-80-3; STN Entry Date Mar. 28, 2006.
SciFinder: CAS Registry No. 1156676-10-6; STN Entry Date Jun. 14, 2009.
SciFinder: CAS Registry No. 1099745-60-4; STN Entry Date Feb. 2, 2009.
Shanghai Library; Institute of Scientific & Technical Information of Shanghai; Amides of *Piper amalago* var. *nigrinodum*; Helen Jacobs, et al.; J. Indian Chem. Soc. vol. 76, Nov.-Dec. 1999, pp. 713-717.
Bioorganic & Medicinal Chemistry Letters 18 (2008) 5451-5455; Discovery of Small Molecule Agonists for the Bombesin Receptor Subtype 3 (BRS-3) based on an Omeprazole Lead; David L. Carlton, et al.; Journal Homepage: www.elsevier.com/locate/bmcl; Elsevier Ltd.
Natural Product Research and Development; Studies on Chemical Constituents of Piper Austrosinense vol. 7 No. 2; Liu Hongyu, et al.; Institute of Medical Plant Development, Chinese Academy of Medical Sciences, Beijing 100094; National Laboratories of Natural and Biomimetic Drugs, Beijing Medical University, Beijing 100083.
School of Pharmaceutical Sciences, Beijing Medical University, Beijing; Wang Shu-Yu, et al.; Department of Chemistry, Peking University, Beijing; Xu Xiao-Jie, et al.; Youji Huaxue, 1988, 8, 217-220; Molecular Shape Analysis and Quantitative Structure-Anticonvulsant Activity Relationships of Cinnamamides.
Phytochemistry; Phytochemistry 70 (2009) 1442-1447; Oxidative Burst Inhibitory and Cytotoxic Amides and Lignans From the Stem Bark of Fagara Heitzii (Rutaceae); Luc Meva'a Mbaze[a], et al.; Journal Homepage: www.elsevier.com/locate/phytochem; Elsevier.
Antifungal and Antioxidant Compounds From the Root Bark of Fagara Zanthoxyloides; Fatima Chaaib, et al.; Original Paper 316.
Computers and Applied Chemistry vol. 21, No. 4 Jul. 2004; The Quantum Study on Structyre-activity Relations of 3, 4-methnyldioxy cassia-acylamide; Niu LiYing, et al. 587-590; Chinese Medicine College, Hebei Medicine University, Shijiangzhuang, 050091, Hebei, China; 2. Department of Chemistry, Hebei Teachers' University, Shijiazhuang, 050016, Hebei, China; Niu Ly, et al.
Chemistry Section, Defence Research Establishment Suffield, Ralston, Alberta Aug. 14, 1968; Partition Coefficients of Some N-alkyl-and N,N-dialkyl-derivatives of some Cinnamamides and Benzalcyanoacetamides in the System Cyclohexane-water; A.D. Delaney[1], et al.
Pharma-Forschungszentrum der Bayer AG, D 5600 Wuppertal-Elberfeld, Deutschland; Wisanin Und Andere Amide Der 5-(Methoxy-4,5-Methylendioxyphenyl)-2,4-Pentadiensäure; S. Linke, et al.

* cited by examiner

SUBSTITUTED CINNAMAMIDE DERIVATIVE, PREPARATION METHOD AND USE THEREOF

CROSS-REFERENCE TO RELATED APPLICATIONS

This application is an U.S. national stage of PCT/CN2012/077549, filed on Jun. 26, 2012, which claims priority to Chinese Patent Application No. 201210123842.7, filed on Apr. 25, 2012 and Chinese Patent Application No. 201110174376.0, filed on Jun. 27, 2011, the contents of which are each incorporated herein by reference in its entirety.

FIELD OF THE INVENTION

The present invention relates to the fields of both organic chemistry and pharmaceutics, in particular to a compound of a general formula (I), the pharmaceutically acceptable acid addition salts of the compound of the general formula (I), the method for preparing thereof, the pharmaceutical composition containing thereof and the use of the compound of the general formula (I) for treating and/or preventing depressive-type mental diseases.

BACKGROUND OF THE INVENTION

Depression is believed to be an affective disorder, a mental disease symptom that is mainly characterized by a depressed mood. Clinically, it is expressed by a series of symptoms, including depressed mood, bradyphrenia, less words, decreased activity and loss interest in work etc. As reported by the WHO, depression has become the fourth largest disease in worldwide. By 2020, it will likely to become the second largest disease, just next to heart diseases. Now, there are about 26 million depression patients in China, only 10% of which, however, can have opportunity to get normal drug therapy. Hence, anti-depressive drugs will certainly have a huge potential market.

As suggested by numerous researches, the change of nerve center monoaminergic neurotransmitters, dopamine and cholinergic, variation of their relevant receptor function and neuroendocrine dysfunction were likely to play an important role in occurrence and development of depression. Up to now, a principle for treating the depression should be focused on adjusting the content of monoamine neurotransmitters in hypothalamus, their receptor function and restoring normal neuroendocrine.

Nowadays, drug therapy is still the main manner for treating depression. It has been confirmed by literatures that the pathogeny of depression is complex, associated with many factors, e.g. social psychology, heredity, biochemical changes of human body and neuroendocrinology. The anti-depressive drug is possible to have various kinds of targets, e.g. receptors, concentration of monoamine neurotransmitters and cytokine. Different anti-depressive drugs take effect through different targets. The first generation of anti-depressive drugs belonged to monoamine oxidase inhibitors. However, the selectivity and irreversible inhibitory effect on enzyme thereof lead to toxic liver injury, which has certain toxic and side effects; therefore, it is gradually replaced by tricyclic anti-depressive drugs. Such common-used medicines include doxepin, amitriptyline and clomipramine etc. Although having a better therapeutic effect on endogenous depression, especially having more than 80% of efficacy for emotional depression, loss of interest and pessimism, these drugs are considered to have higher cardiac toxicity and more adverse reactions. In the late 1980s, selective 5-HT reuptake inhibitor (SSRI) emerged as a kind of novel anti-depressive drug. By now, they have been used as a common first-line anti-depressive drug in Europe and USA, because they maintain the classical effect of anti-depression, and significantly reduce adverse reactions caused by other receptors. Such common-used medicines include fluoxetine, paroxetine, sertraline, citalopram and fluvoxamine etc. They are absorbed through stomach and intestine and metabolized in live, thus cause gastrointestinal dysfunction, and some of them further cause sexual dysfunction. Also, clinical studies showed that it was hard to achieve a satisfactory effect for those synthesized drugs which was designed to direct to single target. Up until now, there has not been developed the ideal anti-depressive drug with better efficacy and less toxic and side effects.

Chinese patent application (Appl. No.: 201010169679.9) disclosed a compound of N-isobutyl-5'-methoxy-3',4'-methylenedioxy cinnamamide, which was a alkaloids extracted from *Piper laetispicum* C. DC, a plant of piperaceae. Its structure is presented below. As shown in animal experiments, the compound of N-isobutyl-5'-methoxy-3',4'-methylenedioxy cinnamamide had significant anti-depressive effect.

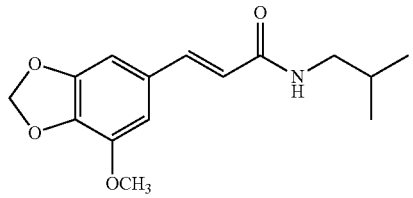 [SMILES: COc1cc(/C=C/C(=O)NCC(C)C)cc2c1OCO2]

N-isobutyl-5'-methoxy-3',4'-methylenedioxy cinnamamide

Actually, there is a limited resource of the plant of *Piper laetispicum* C. DC with a low content of the compound, N-isobutyl-5'-methoxy-3',4'-methylenedioxy cinnamamide therein. The extraction and separation of this compound solely from the plant will be hard to meet the demands of basic research and clinical study. Thus, the present invention focuses on the process of chemically synthesizing N-isobutyl-5'-methoxy-3',4'-methylenedioxy cinnamamide and its derivatives, so as to obtain a drug molecule with a higher anti-depressive activity.

In the present invention, N-isobutyl-5'-methoxy-3',4'-methylenedioxy cinnamamide (I-1) and its derivatives have been synthesized and their anti-depressive activities have been screened out by various types of mice depression models. Eventually, a series of drug molecules having significant anti-depression effects have been found.

DETAILED DESCRIPTION OF THE INVENTION

The objective of the present invention is to provide a compound of a general formula (I) and its pharmaceutically acceptable acid addition salts:

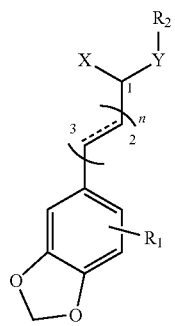
(I)

wherein, $R_1$ is H, OH, F, Cl, Br, I, $OCH_3$, $OCF_3$, $OCHF_2$, $OCH_2F$, $CF_3$, $CHF_2$, $CH_2F$, $CH_3$, $CH_3CH_2$, $CF_3CH_2$, CN, $NO_2$, $NH_2$ or $COOR_3$; wherein said $R_3$ is H, $C_1$~$C_{10}$ straight chain hydrocarbyl, $C_3$~$C_{10}$ branched chain hydrocarbyl, $C_3$~$C_{10}$ cyclic hydrocarbyl or $C_6$~$C_{10}$ aromatic hydrocarbyl;

n is 0, 1, 2 or 3, and the

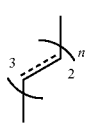

unit contains at least one carbon-carbon single or double bond;

X is =O, =S, H, SH or $SR_3$;

Y is N or $NR_3$, O or S, wherein said $R_3$ is H, $C_1$~$C_{10}$ straight chain hydrocarbyl; $C_3$~$C_{10}$ branched chain hydrocarbyl; $C_3$~$C_{10}$ cyclic hydrocarbyl or $C_6$~$C_{10}$ aromatic hydrocarbyl;

$R_2$ is H, $C_1$~$C_{10}$ straight chain hydrocarbyl, $C_3$~$C_{10}$ branched chain hydrocarbyl, $C_3$~$C_{10}$ cyclic hydrocarbyl, $C_6$~$C_{10}$ aromatic hydrocarbyl, hydroxyalkyl or N-substituted piperazine derivatives group; or $R_2$ is a group which forms tetrahydropyrrolyl, piperidyl or hexamethyleneimino group with the neighboring Y.

Preferably, $R_1$ is —$CF_3$;

n is 0, 1, 2 or 3, and the

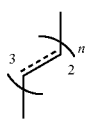

unit contains at least one carbon-carbon single or double bond;

X is =O;

Y is N or NH;

$R_2$ is H, $C_1$~$C_{10}$ straight chain hydrocarbyl, $C_3$~$C_{10}$ branched chain hydrocarbyl, $C_3$~$C_{10}$ cyclic hydrocarbyl, $C_6$~$C_{10}$ aromatic hydrocarbyl, $C_1$~$C_{10}$ hydroxyalkyl or N-substituted piperazine derivatives group; or $R_2$ is a group which forms tetrahydropyrrolyl, piperidyl or hexamethyleneimino group with the neighboring Y.

Another preferably substituted cinnamamide derivative is presented with a structure of the following general formula (II).

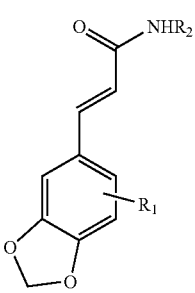
(II)

Wherein, $R_1$ is H, OH, F, Cl, Br, I, $OCH_3$, $OCF_3$, $OCHF_2$, $OCH_2F$, $CF_3$, $CHF_2$, $CH_2F$, $CH_3$, $CH_3CH_2$, $CF_3CH_2$, CN, $NO_2$, $NH_2$ or $COOR_3$; wherein said $R_3$ is $C_1$~$C_{10}$ straight chain hydrocarbyl, $C_3$~$C_{10}$ branched chain hydrocarbyl, $C_3$~$C_{10}$ cyclic hydrocarbyl or $C_6$~$C_{10}$ aromatic hydrocarbyl;

$R_2$ is H, $C_1$~$C_{10}$ straight chain hydrocarbyl, $C_3$~$C_{10}$ branched chain hydrocarbyl, $C_3$~$C_{10}$ cyclic hydrocarbyl, $C_6$~$C_{10}$ aromatic hydrocarbyl, $C_1$~$C_{10}$ hydroxyalkyl or N-substituted piperazine derivatives group.

Most preferably, the structure of the present compound and its pharmaceutically acceptable acid addition salts are represented by the following compounds.

N-isobutyl-5'-methoxy-3',4'-methylenedioxy cinnamamide (I-1)

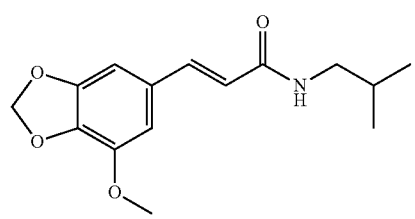
I-1

N-isobutyl-5'-nitro-3',4'-methylenedioxy cinnamamide (I-2)

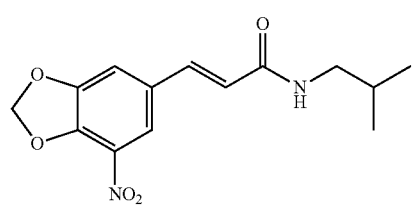
I-2

N-isobutyl-5'-iodo-3',4'-methylenedioxy cinnamamide (I-3)

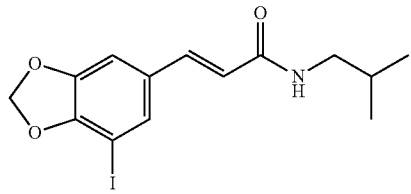

N-isobutyl-5'-chloro-3',4'-methylenedioxy cinnamamide (I-4)

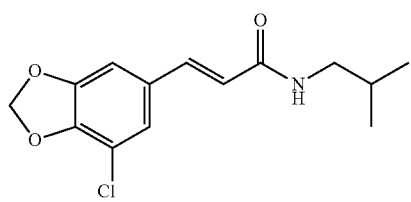

N-isobutyl-5'-trifluoromethyl-3',4'-methylenedioxy cinnamamide (I-5)

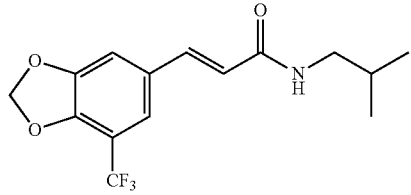

N-isobutyl-5-(5'-methoxy-3',4'-methylenedioxy phenyl)pentadienamide (I-6)

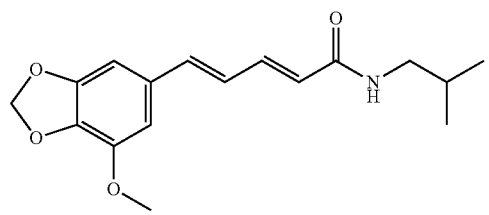 [SMILES: COc1cc(/C=C/C=C/C(=O)NCC(C)C)cc2c1OCO2]

N-isobutyl-3',4'-methylenedioxy cinnamamide (I-7)

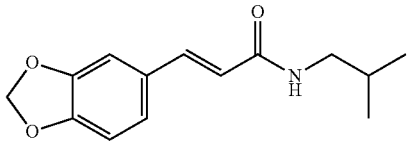

N,N-dimethyl-5'-trifluoromethyl-3',4'-methylenedioxy cinnamamide (I-8)

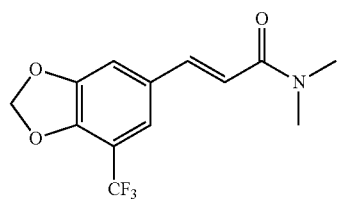

N,N-diethyl-5'-trifluoromethyl-3',4'-methylenedioxy cinnamamide (I-9)

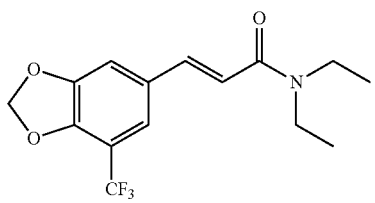

1-(5'-trifluoromethyl-3',4'-methylenedioxy cinnamyl)-piperidine (I-10)

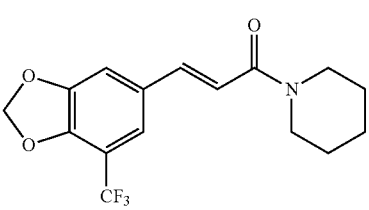

N-isobutyl-3-(5'-trifluoromethyl-3',4'-methylenedi-
oxy phenyl)-propionamide (I-11)

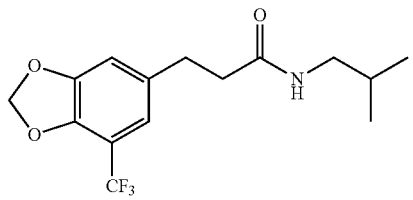

I-11

N-isobutyl-5-trifluoromethyl-3,4-methylenedioxy
benzamide (I-12)

I-12

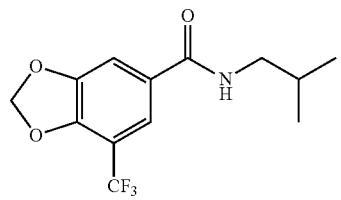

1-(5-trifluoromethyl-3,4-methylenedioxy
benzoyl)-piperidine (I-13)

I-13

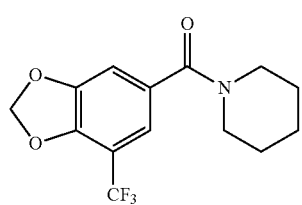

According to the present invention, said pharmaceutically acceptable acid addition salts of the present compounds are prepared by reacting with the following acids: sulfuric acid, hydrochloric acid, hydrobromic acid, phosphoric acid, tartaric acid, fumaric acid, maleic acid, citric acid, acetic acid, formic acid, methanesulfonic acid, p-toluene sulphonic acid, oxalic acid or succinic acid; preferably, said pharmaceutically acceptable acid addition salts of the present compounds are the hydrochloride salts.

In another aspect, the invention provides a method for preparing the compounds of the general formula (I).

Preferably, the compound of the general formula (I) is N-isobutyl substituted cinnamamide derivative. The compound of the general formula (I) is prepared by the following synthetic routes:

The substituted cinnamic acid derivative is obtained by a Wittig reaction or Wittig-Horner reaction between a substituted piperonal derivative and ethoxyformyl methylene triphenyl phosphine or triethyl phosphonoacetate.

The obtained substituted cinnamic acid derivative is further acylated to obtain an acylated derivative (including acyl halide, azide, anhydride, active ester) thereof, and then the acylated derivative is reacted with an organic amine to obtain an amide derivative; Alternatively, the substituted cinnamic acid derivative is reacted with an organic amine and a condensing agent (HATU, HBTU, EDCI, DCC etc.) to obtain an amide derivative.

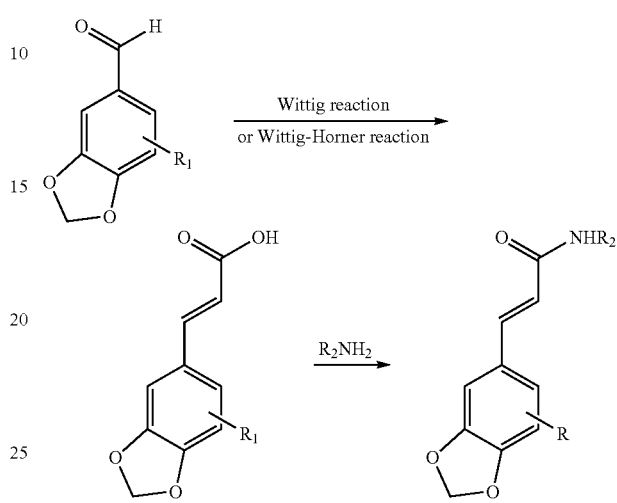

According to the present invention, the most convenient synthetic method is to obtain an amide compound by an amidation reaction of the acid corresponding to the final product.

The preferable structure of 5'-trifluoromethyl-3',4'-methylenedioxy cinnamamide derivative is prepared by following synthetic routes:

Using 5'-trifluoromethyl-3',4'-methylenedioxy cinnamic acid as a starting material to obtain an acylated derivative (including acyl halide, azide, anhydride, active ester) thereof, and then reacting the acylated derivative with an organic amine to obtain an amide derivative; Alternatively, reacting 5'-trifluoromethyl-3',4'-methylenedioxy cinnamic acid with an organic amine and a condensing agent (HATU, HBTU, EDCI, DCC etc.) to obtain an amide derivative;

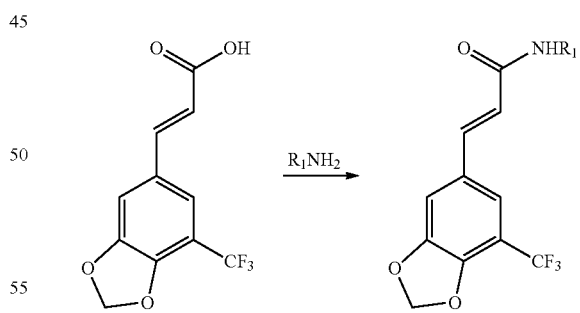

Preferably, the acyl halide is used to be directly acylated.

According to the present invention, said pharmaceutically acceptable acid addition salts of the present compounds are prepared by a conventional acid-base neutralization reaction. For example, the corresponding acid addition salts of the present invention are prepared by reacting the present compound with the following acids: sulfuric acid, hydrochloric acid, hydrobromic acid, phosphoric acid, tartaric acid, fumaric acid, maleic acid, citric acid, acetic acid, formic acid, methane sulfonic acid, p-toluene sulphonic acid, oxalic acid or succinic acid, preferably, said pharmaceutically acceptable acid addition salts of the present compounds are the hydrochloride salts.

In another aspect of the present invention, the pharmaceutical compositions containing said compound of the present invention or their pharmaceutically acceptable acid addition salts are provided.

According to the present invention, the pharmaceutical compositions can be prepared into any dosage forms. The dosage forms include: tablets, e.g. sugar-coated tablets, film-coated tablets, enteric-coated tablets or sustained released tablets; capsules, e.g. hard capsules, soft capsules or sustained released capsules; oral solutions; buccal tablets; granules; granules taken after dissolving in boiling water; pills; pulvis; pastes, e.g. ointments, plasters; pellets; suspensions; powders; liquors, e.g. injections; suppositories; creams; sprays; drops and patches.

According to the present invention, the compound can be preferably prepared into a formulation in unit dosage form.

According to the present invention, the composition comprises 0.1~1000 mg of the said compound as an active ingredient per unit dosage form, and the balanced is pharmaceutically acceptable excipient(s). Said pharmaceutically acceptable excipient(s) account for 0.01~99.99 wt % of the total weight of the formulation.

According to the present invention, the medical usage and the dosage of said composition are determined by patients' conditions, e.g. 1~3 times per day and 1~10 tablets per time.

According to the present invention, said composition can be prepared into orally-administered dosage form or injections.

Wherein, said orally-administered dosage form is selected from one kind of the following: capsules, tablets, drop pills, granules, concentrated pills and oral solutions.

Wherein, said injections are selected from one kind of the following: injection solutions, lyophilized powder for injection and water injections.

According to the present invention, said orally-administrated dosage form of the present pharmaceutical composition generally contains conventional excipient(s), e.g. binding agents, bulking agents, diluents, tablet-pressing agents, lubricants, disintegrating agents, colorants, flavoring agents, wetting agents, and if necessary, the tablets can be coated.

Suitable bulking agents include cellulose, mannitol, lactose and other analogous bulking agents. Suitable disintegrating agents include starch, polyvinylpyrrolidone (PVP) and starch derivatives (preferably sodium starch glycollate). Suitable lubricants include, such as magnesium stearate. Suitable wetting agents include sodium dodecyl sulfate.

Usually, the orally-administrated solid preparations can be prepared by conventional methods, such as blending, filling and tablet-pressing, etc. Being blended repeatedly allows the active substance distribute uniformly into those compositions having a large amount of bulking agent.

According to the present invention, the oral liquid preparations can be, for example water-soluble or oil-soluble suspensions, solutions, emulsions, syrups or elixirs, or dried products that can be reconstituted with water or other suitable carriers before using. The liquid preparations can contain conventional additives, for example, suspending agents, e.g. sorbitol, syrup, methylcellulose, gelatin, hydroxyethyl cellulose, carboxymethyl cellulose, aluminum stearate gel or hydrogenated edible fat; emulsifying-agents, e.g. lecithin, sorbitan monoleate or arabic gum; non-aqueous carriers which can be edible oil, e.g. almond oil, fractionated coconut oil, esters of glycerol, propylene glycol or ethanol; and preservatives, e.g. methyl paraben, nipasol or sorbic acid. And if necessary, conventional scenting agents or colorants can be included.

As for the injections, the prepared liquid unit dosage form contains the active component(s) of the present invention and sterile carrier(s). According to the type of the carrier(s) and the concentration of the active component(s), said active component(s) can be dissolved or suspended. Generally, the solutions are prepared by dissolving the active component(s) in the carriers, sterilizing by filtering, loading into a suitable vial or ampoule, and sealing. Some pharmaceutically acceptable vehicles, e.g. local anesthetics, preservatives and buffering agents can also be added into the carriers. In order to improve the stability, the composition of the present invention can be frozen after being loaded into the vial and then treated in vacuum to remove water.

According to the present invention, said pharmaceutical composition is prepared into a formulation into which the pharmaceutically acceptable carriers can be added optionally. Said carriers are selected from sugar alcohol, e.g. mannitol, sorbitol, xylitol; amino acids, e.g. cysteine hydrochloride, methionine, glycine; EDTA disodium, EDTA calcium sodium; inorganic salts, e.g. carbonates, phosphates of the monovalent alkali metals or aqueous solutions thereof, sodium chloride, potassium chloride, sodium pyrosulfite, sodium bisulfite, sodium thiosulfate, calcium carbonate, calcium bicarbonate; stearates, e.g. calcium stearate, magnesium stearate; inorganic acids, e.g. hydrochloric acid, sulfuric acid, phosphoric acid; organic acids, e.g. acetic acid, Vitamin C; organic acid salts, e.g. acetates, sodium lactate; oligosaccharides, polysaccharides, celluloses and derivatives thereof, e.g. maltose, glucose, fructose, dextran, sucrose, lactose, cyclodextrin (such as β-cyclodextrin), starch; mercaptoacetic acid; silicon derivatives; alginate; gelatin; PVP, glycerol; Tween-80; agar; surfactants; polyethylene glycol; phospholipids materials; Kaolin; talc powder etc.

According to the present invention, said pharmaceutical composition may be applied in combination with other anti-depressive drugs. That is to say, except the compound of the present invention, there are one or more kinds of anti-depressive drugs which is (are) clinically used for prevention and treatment of mental diseases, e.g. nefazodone, sulpiride, alprazolam, serenase, buspirone, tandospirone, methylphenidate, fluoxetine, paroxetine, sertraline, citalopram, lexapro, fluvoxamine, reboxetine, venlafaxine, fluanxol, melitracene and neurostan etc.

According to the present invention, as shown in animal experiments, the substituted cinnamamide and the derivatives thereof can significantly shortened immobility time in the forced swimming test and in the tail suspension test of mice, which are the two acquired-behavioral despair animal models of depression. They have the effect of antagonizing the activity of reserpine in consuming monoamine. Thus, the substituted cinnamamide and the derivatives thereof can be used as a drug for treatment and prevention of depressive-type mental diseases.

In another aspect of the present invention, the use of the compound of the general formula (I) in preparation of a medicine for preventing and treating depressive-type mental diseases is provided.

According to the present invention, the beneficial effects of the compound and the composition for preventing and treating mental diseases are confirmed via the following experimental data.

Test 1 A "Acquired Despair" Depression Model of Tail Suspension Test in Mice

1 Material
1.1 Reagents

Compounds of I-1, I-2, I-3, I-4, I-5, I-6, I-7, I-8, I-9, I-10, I-11, I-12 and I-13 were synthesized in light of the method of the present invention with a purity of more than 95%. They were added into 2% Tween-80 aqueous solution to obtain a solution containing 1 mg/ml of the drug compound before use.

Fluoxetine hydrochloride was manufactured by Patheon Inc. (France) and separately packaged by Eli Lilly (Suzhou) Pharmaceutical Inc. with a specification of 20 mg/pill and a batch number of 81958. Before experiment, it was dissolved into 2% Tween-80 aqueous solution to prepare a solution containing 1 mg/ml of the drug compound.

1.2 Animals

C57BL/6 mice were purchased from Beijing Vital River Experimental Animal Co. Ltd. Animal certification number was SCXK (Beijing) 2006-0009.

1.3 Apparatus

YLS-1A multi-functional mice autonomic activity recorder was provided by Shandong Institute of Medical Instruments.

2. Method 240 male C57BL/6 mice with a weight of 18~22 g at the age of 6~8 weeks are feed adaptive for 2~3 days.

Experiment 1

110 mice were randomly selected to observe the number of their autonomic activity. The mice was placed into the YLS-1A multi-functional mice autonomic activity recorder, and after 1 min of adaption, the mice's activity was counted within a time period from the end of $1^{st}$ min to $4^{th}$ min. 96 mice with the number of autonomic activity between 70~140 were screened out, divided randomly into 8 groups, and intragastrically administrated with the drug compounds at a dose listed in Table 1, one time daily for 7 days consecutively. The solvent control group was administrated with 2% Tween-80 aqueous solution in the same volume. All mice were placed into the autonomic activity recorder 30 min after administration at $6^{th}$ day. After 1 min of adaption, the mice's activity was counted within a time period from the end of $1^{st}$ min to $4^{th}$ min.

30 min after administration at $7^{th}$ day, the mice was fixed on a sustainer with a rubberized cloth at 1 cm close to the end of the tail of mice, making the mice hanged upside down. The head of the mice was about 30 cm above the table and its sight was separated from the neighboring mouse with a plate. Usually, the mice might manage to struggle in hopes of overcoming the abnormal body position. After a period of time, however, the mice showed immobility episodically, displaying hopelessness. The accumulated immobility time within 6 min of each mouse was observed, which was regarded as "despair time". Wherein, the immobility is referred to that the limbs of mice do not move except taking respiration.

Experiment 2

130 mice were randomly selected to observe the number of their autonomic activity. The method was the same with that of Experiment 1. 108 mice with the number of autonomic activity between 70~140 were screened out, divided randomly into 9 groups, and intragastrically administrated with the drug compounds at a dose listed in Table 2, one time daily for 7 days consecutively. The solvent control group was administrated with 2% Tween-80 aqueous solution in the same volume. 30 min after administration at $6^{th}$ day, the number of the autonomic activity of each mouse was observed. 30 min after administration at $7^{th}$ day, the immobility time in tail suspension test was observed. The method was the same with that in Experiment 1.

Statistics:

SPSS10.0 analytical software was used and the results were analyzed with one-way Anova method to compare the inter-group significance.

3. Results

Experiment 1 was used to evaluate the effect of compounds I-1, I-2, I-3, I-4, I-5, I-6 on the number of the autonomic activity and immobility time of mice in tail suspension test. As shown in Table 1, compared with the solvent control group, one week of intragastric administration of fluoxetine hydrochloride at a dose of 10 mg/kg had no effect on mice autonomic activity and could reduce the immobility time in tail suspension test significantly ($p<0.01$). Intragastric administration of compounds I-4 or I-5 at a dose of 10 mg/kg could also remarkably reduce the immobility time of the mice in tail suspension test ($p<0.05$, $p<0.01$), but had no affect the autonomic activity of mice. As for other treating groups, the immobility time of the mice in tail suspension test was reduced to different degrees, but had no statistical difference. Compared with I-1, I-4 or I-5 had a better effect on antagonize immobility of the mice in tail suspension test ($p<0.05$).

TABLE 1

Effect of different compounds on the number of the autonomic activity and the immobility time of mice in the tail suspension test

| Groups | Dosages | Number of the mice | Number of Autonomic activity (time) | Immobility time in tail suspension test (s) |
|---|---|---|---|---|
| Solvent control | — | 12 | 107.75 ± 8.38 | 193.11 ± 41.69 |
| fluoxetine hydrochloride | 10 mg/kg | 12 | 121.75 ± 24.14 | 131.14 ± 28.76**Δ |
| I-1 | 10 mg/kg | 12 | 113.92 ± 14.24 | 180.10 ± 18.26 |
| I-2 | 10 mg/kg | 12 | 102.00 ± 26.24 | 169.69 ± 38.10 |
| I-3 | 10 mg/kg | 12 | 94.42 ± 23.97 | 173.14 ± 32.39 |
| I-4 | 10 mg/kg | 12 | 94.75 ± 28.53 | 155.29 ± 31.81*Δ |
| I-5 | 10 mg/kg | 12 | 94.75 ± 23.98 | 147.54 ± 35.72**Δ |
| I-6 | 10 mg/kg | 12 | 98.83 ± 17.56 | 164.82 ± 23.04 |

Note:
compared with the solvent control group. *$p < 0.05$, **$p < 0.01$;
compared with I-1, $^Δp < 0.05$.

Experiment 2 was used to evaluate the effect of the compounds I-5, I-8, I-9, I-10, I-11, I-12 and I-13 on the number of autonomic activity of the mice and the immobility time in tail suspension test. As shown in Table 2, compared with the solvent control group, one week of intragastric administration of I-5, I-9, I-10, I-11, I-12, I-13 at a dose of 10 mg/kg could reduce the immobility time of the mice in tail suspension test significantly (p<0.01), but had no effect on the autonomic activity of the mice. It was illustrated that these compounds had a certain anti-depression activity without an action of exciting central nervous system.

TABLE 2

Effect of different compounds on the number of the autonomic activity and the immobility time of the mice in tail suspension test

| Groups | Dosages | Number of the mice | Number of Autonomic activity (time) | Immobility time in tail suspension test (s) |
|---|---|---|---|---|
| Solvent control | — | 12 | 94.50 ± 19.55 | 204.05 ± 33.86 |
| fluoxetine hydrochloride | 10 mg/kg | 12 | 102.0 ± 14.91 | 123.58 ± 30.44** |
| I-5 | 10 mg/kg | 12 | 99.40 ± 19.67 | 117.34 ± 32.78** |
| I-8 | 10 mg/kg | 12 | 84.00 ± 21.81 | 194.39 ± 39.14 |
| I-9 | 10 mg/kg | 12 | 83.60 ± 22.68 | 139.70 ± 48.62** |
| I-10 | 10 mg/kg | 12 | 95.30 ± 15.06 | 121.91 ± 22.75** |
| I-11 | 10 mg/kg | 12 | 86.60 ± 23.08 | 145.32 ± 33.78** |
| I-12 | 10 mg/kg | 12 | 93.20 ± 19.54 | 136.44 ± 53.28** |
| I-13 | 10 mg/kg | 12 | 87.40 ± 22.39 | 122.76 ± 39.34** |

Note:
compared with the solvent control group. **p < 0.01.

Test 2 A Depression Model Test of Anti-Blepharoptosis Caused by Reserpine
1 Material
1.1 Reagents Compounds I-1, I-2, I-3, I-4, I-5, I-6, I-7, I-8, I-9, I-10, I-11, I-12 and I-13 were synthesized in accordance with the method of the present invention (purity >95%). 2% Tween-80 aqueous solution was added to prepare a solution containing 1 mg/ml of the drug compound.

Fluoxetine hydrochloride was manufactured by Patheon Inc. (France) and separately packaged by Eli Lilly (Suzhou) Pharmaceutical Inc. with a specification of 20 mg/pill and a batch No. of 81958. Before experiment, it was dissolved into 2% Tween-80 aqueous solution to prepare a solution containing 1 mg/ml of the drug compound.

Reserpine injection was purchased from Shanghai Fudan Fuhua Pharmaceutical Co., Ltd. with a specification of 1 mg/ml and a batch number of x070302.

1.2 Animals

C57BL/6 mice was purchased from Beijing Vital River Experimental Animal Co. Ltd. Animal certification number was SCXK (Beijing) 2006-0009.

1.3 Apparatus

YLS-1A multi-functional mice autonomic activity recorder was provided by Shandong Institute of Medical Instruments.

2. Method 240 male C57BL/6 mice with a weight of 18~22 g at the age of 6~8 weeks are feed adaptive for 2~3 days.

Experiment 1

120 male C57BL/6 mice were randomly selected to observe the number of their autonomic activity. The mice was placed into the YLS-1A multi-functional mice autonomic activity recorder, and after 1 min of adaption, the activity of the mice was counted within a time period from the end of $1^{st}$ min to $4^{th}$ min. 96 mice with the number of autonomic activity between 70~140 were screened out, divided randomly into 8 groups, and intragastrically administrated with the drug compounds at a dose listed in Table 3, one time daily for 7 days consecutively. The solvent control group was administrated with 2% Tween-80 aqueous solution in the same volume. Except the normal control group, 30 min after the last administration, each group was injected intraperitoneally with reserpine at a dose of 4 mg/kg. Next, akinesia, blepharoptosis and shell temperature were observed.

I Akinesia: one hour after intraperitoneal injection of reserpine, the mice were placed at the center of a circle with a diameter of 7.5 cm for a 15-second observation to calculate the "out-of-circle" ratio.

II Blepharoptosis: one hour after intraperitoneal injection of reserpine, the eye closure of mice was observed and scored by the following standard: eyelids open, 0; eyelids ¼ closed, 1; eyelids ½ closed, 2; eyelids ¾ closed, 3; eyelids closed completely, 4.

III Shell temperature: two hours after intraperitoneal injection of reserpine, the shell temperature of the abdomen of the mice was measured.

Experiment 2

120 C57BL/6 mice were randomly selected to observe the number of their autonomic activity. The method was the same with that of Experiment 1. 100 mice with the number of autonomic activity between 70~140 were screened out, divided randomly into 10 groups, and intragastrically administrated with the drug compounds at a dose listed in Table 4, one time daily for 7 days consecutively. The mice in the normal group and the solvent control group were administrated with 2% Tween-80 aqueous solution in the same volume. Except the normal control group, 30 min after the last administration, each group was injected intraperitoneally with reserpine at a dose of 4 mg/kg. Next, akinesia, blepharoptosis and shell temperature were observed. Observation method was the same with that of Experiment 1.

Statistics:

SPSS10.0 analytical software was used and the results were analyzed with one-way Anova method to compare the inter-group significance.

3 Results

Reserpine reversal is believed to be a vesicle re-uptake inhibitor, which makes the transmitters out of the vesicle and further leads to easy degradation of the transmitters by monoamine oxidase. Thus, NE, E, DA, 5-HT and the like are depleted, which results in physiological or behavioral changes, consequently, depression symptoms are observed.

As shown in Experiment 1, after administration of reserpine, akinesia, blepharoptosis and reduced shell temperature were observed. Compared with the solvent control group, the positive drug fluoxetine hydrochloride (10 mg/kg) could obviously increase mice "out-of-circle" ratio and shell temperature, and significantly reduce the degree of eye closure of the mice ($p<0.01$). Compared with the solvent control group, blepharoptosis, "out-of-circle" ratio and shell temperature were improved significantly ($p<0.05$, $p<0.01$) in groups of I-1, I-2, I-3, I-4, I-5, I-6. Compared with I-1, the degree of eye closure of the mice in groups I-3, I-4, I-5 were reduced ($p<0.01$); "out-of-circle" ratio in I-2, I-3, I-4, I-5, I-6 groups increased markedly ($p<0.05$). Compounds I-4 and I-5 had the best effect on improving akinesia, blepharoptosis and shell temperature.

decreased remarkably ($p<0.01$). It was illustrated that the mice depression model induced by intraperitoneal injection of reserpine was successful. Compared with the solvent control group, the positive drug fluoxetine hydrochloride at a dose of 10 mg/kg could improve the "out-of-circle" ratio obviously, and significantly reduce the degree of eye closure and raise the shell temperature ($p<0.01$). Compounds I-1, I-8, I-9, I-11, I-12 and I-13 at a dose of 10 mg/kg could remarkably improve blepharoptosis, shell temperature and "out-of-circle" ratio, and the improvement was statistically significant ($p<0.05$, $p<0.01$). Compound I-10 at a dose of 10 mg/kg could improve blepharoptosis of the mice significantly ($p<0.01$), ameliorate the shell temperature and "out-of-circle" ratio to a certain degree but without statistically significant difference. Compared with Compound I-1, compounds I-11, I-12 and I-13 had significantly improved effect on blepharoptosis, shell temperature and "out-of-circle" ratio of the mice ($p<0.05$, $p<0.01$), and I-9 and I-10 had an

TABLE 3

Effect of each compound on the eye-closure and akinesia induced by reserpine (±SD)

| Groups | Dosage | Number of the mice | Degree of eye-closure | Change in the shell temperature (ΔT ° C.) | "out-of-circle" ratio |
|---|---|---|---|---|---|
| Solvent control | — | 12 | 3.50 ± 0.52 | 3.51 ± 0.37 | 0% |
| fluoxetine hydrochloride | 10 mg/kg | 12 | 1.42 ± 1.38**Δ | 1.89 ± 0.21* | 58%Δ |
| I-1 | 10 mg/kg | 12 | 2.67 ± 0.89* | 2.05 ± 0.24* | 17% |
| I-2 | 10 mg/kg | 12 | 1.67 ± 1.30** | 1.60 ± 0.18* | 83%Δ |
| I-3 | 10 mg/kg | 12 | 1.00 ± 1.13**ΔΔ | 1.72 ± 0.26* | 92%Δ |
| I-4 | 10 mg/kg | 12 | 0.17 ± 0.39**ΔΔ | 1.51 ± 0.31* | 100%Δ |
| I-5 | 10 mg/kg | 12 | 0.42 ± 0.79**ΔΔ | 1.32 ± 0.16* | 92%Δ |
| I-6 | 10 mg/kg | 12 | 2.08 ± 1.68* | 1.84 ± 0.22* | 67%Δ |

Note:
compared with the solvent control group, *$p < 0.05$, **$p < 0.01$;
compared with I-1, $^Δp < 0.05$, $^{ΔΔ}p < 0.01$.

Experiment 2 evaluated the antagonistic effect of compounds I-1, I-8, I-9, I-10, I-11, I-12 and I-13 by intraperitoneal injection of reserpine. As shown in Table 4, compared with the normal group, the degree of eye closure of the mice in the solvent control group was increased significantly ($p<0.01$), but the shell temperature and "out-of-circle" ratio increased improvement on blepharoptosis ($p<0.05$). In terms of the improvement in eye closure and shell temperature of the mice, I-13 had a better effect to a certain degree than that of fluoxetine ($p<0.05$). In terms of the improvement in blepharoptosis, shell temperature and "out-of-circle" ratio of the mice, I-11, I-12 and I-13 had better effects.

TABLE 4

Effect of each compound on the eye-closure, akinesia and the shell temperature induced by reserpine (±SD)

| Groups | Dosage | Number of the mice | Degree of eye-closure | Change in the shell temperature (T ° C.) | "out-of-circle" ratio |
|---|---|---|---|---|---|
| Normal group | — | 10 | 0.00 ± 0.00 | 32.83 ± 0.54 | 100% |
| Solvent control group | — | 10 | 4.00 ± 0.00 | 26.05 ± 0.44ΔΔ | 0%ΔΔ |
| fluoxetine hydrochloride | 10 mg/kg | 10 | 2.00 ± 1.33** | 29.20 ± 0.54** | 50%* |
| I-1 | 10 mg/kg | 10 | 2.91 ± 0.75* | 27.80 ± 0.61*## | 10%# |
| I-8 | 10 mg/kg | 10 | 2.30 ± 1.64** | 27.60 ± 0.88*## | 40%*† |
| I-9 | 10 mg/kg | 10 | 1.80 ± 1.23**† | 28.70 ± 1.78** | 30% |
| I-10 | 10 mg/kg | 10 | 1.80 ± 1.32**† | 27.15 ± 1.20## | 30% |
| I-11 | 10 mg/kg | 10 | 1.40 ± 0.97**†† | 30.20 ± 0.95**#†† | 50%*† |
| I-12 | 10 mg/kg | 10 | 1.50 ± 1.18**† | 30.65 ± 1.16**#†† | 70%*† |
| I-13 | 10 mg/kg | 10 | 0.90 ± 0.88**#†† | 30.20 ± 0.95**#†† | 70%*† |

Note:
compared with the normal group, $^{ΔΔ}p < 0.01$;
compared with the solvent control group, *$p < 0.05$, **$p < 0.01$;
compared with fluoxetine hydrochloride group, #$p < 0.05$, ##$p < 0.01$;
compared with I-1, †$p < 0.05$, ††$p < 0.01$.

Test 3 Forced Swimming Experiment in Mice

1 Material 1.1 Reagents

Compounds I-5, I-10, I-13 were synthesized in accordance with the method of the present invention (purity>95%). 2% Tween-80 aqueous solution was added to prepare a solution containing 1 mg/ml of the drug compound.

Fluoxetine hydrochloride was manufactured by Patheon Inc. (France) and separately packaged by Eli Lilly (Suzhou) Pharmaceutical Inc. with a specification of 20 mg/pill and a batch number of 81958. Before experiment, it was dissolved into 2% Tween-80 aqueous solution to prepare a solution containing 1 mg/ml of the drug compound.

1.2 Animals

C57BL/6 mice were purchased from Beijing Vital River Experimental Animal Co. Ltd. Animal certification number was SCXK (Beijing) 2006-0009.

1.3 Apparatus

YLS-1A multi-functional mice autonomic activity recorder was provided by Shandong Institute of Medical Instruments.

2. Method

After 1~2 days of adaptive feed, 80 male C57BL/6 mice, aged 6~8 weeks and weighing 18~22 g, were placed into the YLS-1A multi-functional mice autonomic activity recorder. After 1 min of adaption, the activity of the mice was counted within a time period from the end of $1^{st}$ min to $4^{th}$ min. 60 mice with the number of autonomic activity between 70~140 were screened out, divided randomly into 6 groups, and intragastrically administrated with the drug compounds at a dose listed in Table 5, one time daily for 7 days consecutively. The solvent control group was administrated with 2% Tween-80 aqueous solution in the same volume. After the administration at $6^{th}$ day, the mice were placed into a cylindrical aquarium with a water depth of 10 cm and 25° C. to force the mice to swim. After 15 min, the mice were taken out, dried and returned to the cage. 24 hours later, 30 min after the last intragastrical administration, the mice were placed into a glass bottle with a diameter of 10 cm, a height of 30 cm and a water depth of 10 cm, and the temperature of the water in the bottle was at 25° C. The mice were separated with an opaque partition, so as not to influence each other. After 2 min of adaption, an accumulated immobility time from the end of $2^{nd}$ min to $6^{th}$ min was recorded. Said immobility status is referred to that the mice stop struggling or float on the surface of water, and the whole body shows slightly curled with only small limb movements to keep their head floating on the water with their nostrils exposed to the air.

Statistics:

SPSS10.0 analytical software was used and the results were analyzed with one-way Anova method to compare the inter-group significance.

3 Results

As shown in the results, compared with the solvent control group, compounds I-5, I-10, I-13 had an effect of shortening the immobility time within the dosage range in the forced swimming test in mice. It was statistically significant ($p<0.05$, $p<0.01$). I-5 showed a dose-dependent effect on the immobility time in the forced swimming test in mice.

TABLE 5

Effect of the derivatives on the immobility time of the forced swimming test in mice

| Groups | Dosage | Immobility time in the forced swimming test in mice(s) |
|---|---|---|
| Solvent control group | — | 139.05 ± 25.09 |
| Fluoxetine hydrochloride | 10 mg/kg | 98.96 ± 32.43* |
| I-5 low dose group | 5 mg/kg | 91.20 ± 43.09* |
| I-5 high dose group | 10 mg/kg | 78.58 ± 35.70** |
| I-10 | 10 mg/kg | 83.07 ± 31.03** |
| I-13 | 10 mg/kg | 76.00 ± 32.32** |

Note:
compared with the solvent control group, *$p < 0.05$, **$p < 0.01$.

Based on the aforesaid experiments, the following conclusion can be drawn:

1. In the "acquired despair" depression model of tail suspension test in mice, administration of compounds I-4, I-5, I-9, I-10, I-11, I-12 and I-13 at a dose of 10 mg/kg for 7 days can significantly shorten the immobility time in the tail suspension test in mice.

2. In depression model test of anti-blepharoptosis caused by reserpine, administration of compounds I-4, I-5, I-8, I-9, I-10, I-11, I-12 and I-13 at a dose of 10 mg/kg for 7 days has an effect of antagonizing the decrease of shell temperature, akinesia and improving the degree of eye closure of mice induced by reserpine, thus indicates that the compounds of the present invention have a modulating effect on the re-uptake of 5-HT, NE and DA.

3. In the forced swimming test in mice, I-5, I-10 and I-13 of the present compound can shorten the immobility time in the forced swimming test, and I-5 showed a dose-dependent effect on the immobility time in the forced swimming test in mice.

4. Compared with the pharmacologic effect of I-1, the anti-depression effect of I-4, I-5, I-9, I-10, I-11, I-12 and I-13 in the tested model at the tested dose increased to some degree.

In summary, said substituted cinnamamide derivatives of the present invention was confirmed to have a better anti-depression activity than the one in the prior art.

DETAILED DESCRIPTION OF THE PREFERRED EMBODIMENTS

The following examples are given only for purpose of illustration of the present invention. The synthesis and relevant structure identification data of typical compounds are presented in the following examples. The following examples are given only for purpose of illustration and do not intend to limit the scope of the invention in any way. Any simple improvement in accordance with the essence of the present invention should be regarded to be within the protection scope of the present invention.

Example 1 N-isobutyl-5'-methoxy-3',4'-methylenedioxy cinnamamide (I-1)

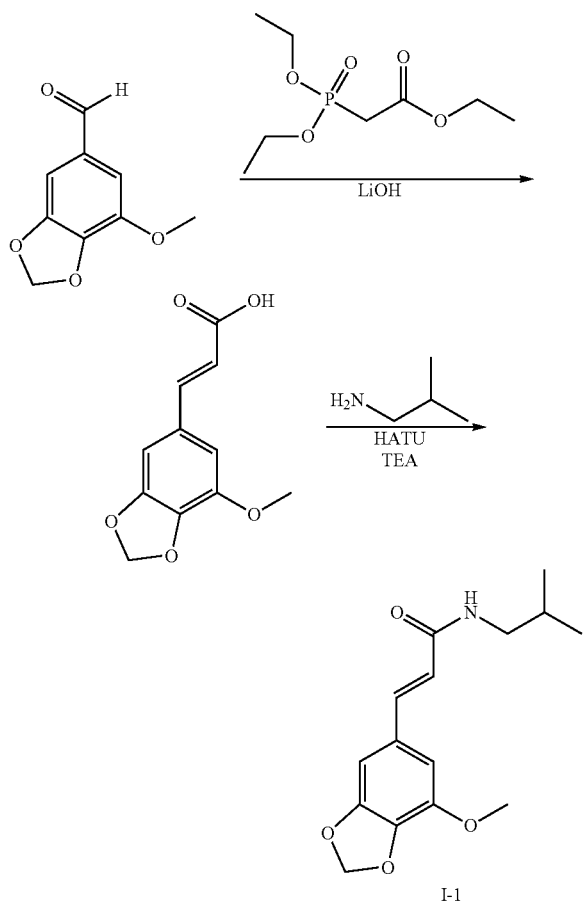

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen.

3,4-methylenedioxy-5-methoxybenzaldehyde (200 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a light-yellow solid to be precipitated. The solid was collected through filtration under reduced pressure, and then a vacuum drying method was used to obtain the intermediate of 5'-methoxy-3',4'-methylenedioxy cinnamic acid (180 mg, 74%).

5'-methoxy-3',4'-methylenedioxy cinnamic acid (210 mg, 0.81 mmol), isobutenamine (71 mg, 0.97 mmol) and triethylamine (122 mg, 1.2 mmol) were dissolved in 10 ml anhydrous dichloromethane, stirred for 15 min under the condition of an ice bath, and slowly added with HATU (368 mg, 0.97 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N-isobutyl-5'-methoxy-3',4'-methylenedioxy cinnamamide (160 mg, 71%).

$^1$H NMR (CDCl$_3$, 400 MHz): δ 7.50 (1H, d, J=15.6 Hz), 6.72 (1H, d, J=1.2 Hz), 6.67 (1H, d, J=1.6 Hz), 6.25 (1H, d, J=15.6 Hz), 6.00 (2H, s), 5.69 (1H, br), 3.91 (3H, s), 3.22 (2H, t, J=6.8 Hz), 1.84 (1H, m), 0.96 (3H, s), 0.95 (3H, s);

$^{13}$C NMR (CDCl$_3$, 100 MHz) δ 166.19, 149.49, 143.85, 140.90, 136.93, 129.97, 119.64, 109.18, 102.05, 101.04, 56.83, 47.33, 28.87, 20.38;

ESI-MS: 278.1 [M+H]$^+$

Example 2 N-isobutyl-5'-nitro-3',4'-methylenedioxy cinnamamide (I-2)

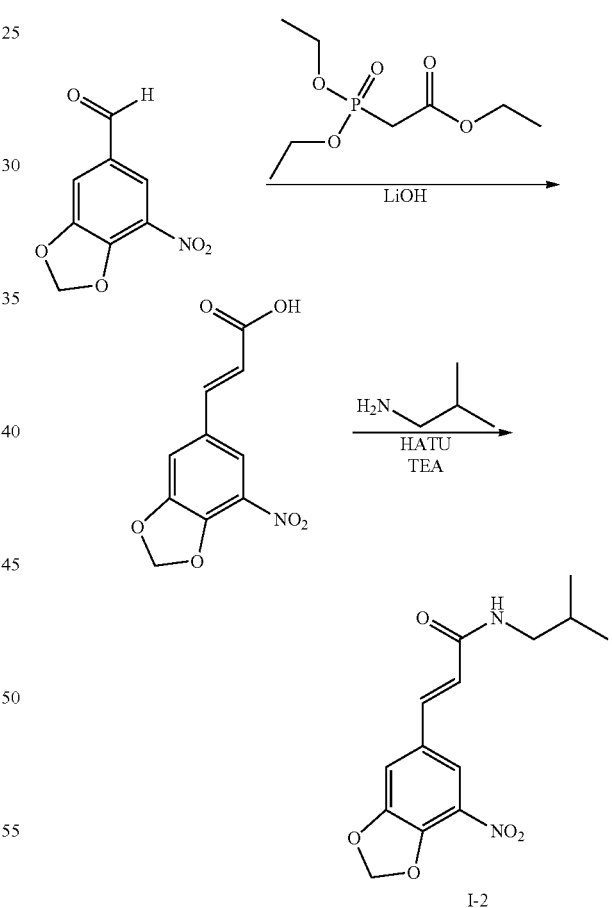

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen. 3,4-methylenedioxy-5-nitrobenzaldehyde (215 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a yellow solid to be precipitated. The solid was collected through filtration under reduced pressure, and then a vacuum drying method was used to obtain the intermediate of 5'-nitro-3',4'-methylenedioxy cinnamic acid (190 mg, 73%).

5'-nitro-3',4'-methylenedioxy cinnamic acid (190 mg, 0.80 mmol), isobutenamine (71 mg, 0.97 mmol) and triethylamine (122 mg, 1.2 mmol) were dissolved in 10 ml anhydrous dichloromethane, stirred for 15 min under the condition of an ice bath and slowly added with HATU (368 mg, 0.97 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N-isobutyl-5'-nitro-3',4'-methylenedioxy cinnamamide (140 mg, 60%).

$^1$H NMR (CDCl$_3$, 400 MHz): δ 7.75 (1H, d, J=1.2 Hz), 7.53 (1H, d, J=15.2 Hz), 7.19 (1H, d, J=1.6 Hz), 6.36 (1H, d, J=15.6 Hz), 6.26 (2H, s), 5.72 (1H, br), 3.23 (2H, t, J=6.8 Hz), 1.85 (1H, m), 0.97 (3H, s), 0.96 (3H, s);

$^{13}$C NMR (CDCl$_3$, 100 MHz): δ 165.32, 151.37, 144.62, 138.53, 132.27, 129.83, 122.31, 117.12, 111.64, 104.20, 47.42, 28.23, 20.36;

ESI-MS: 293.1 [M+H]$^+$

Example 3 N-isobutyl-5'-iodo-3',4'-methylenedioxy cinnamamide (I-3)

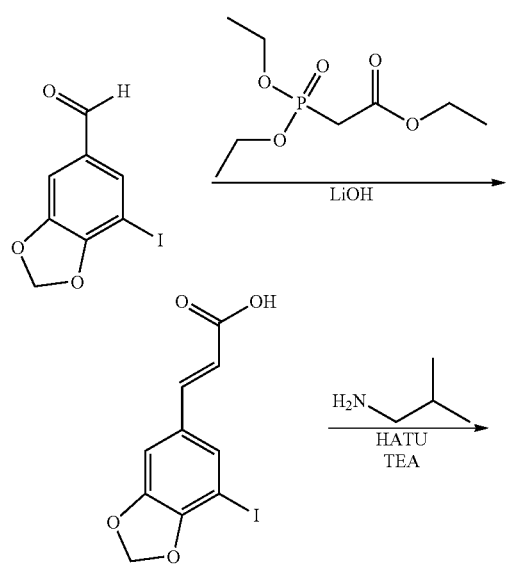

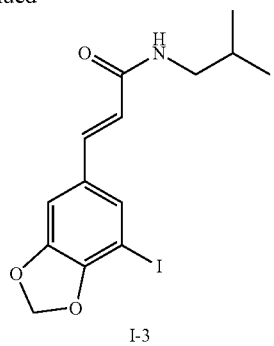

I-3

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen. 3,4-methylenedioxy-5-iodobenzaldehyde (300 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a yellow solid to be precipitated. The solid was collected through filtration under reduced pressure, and then a vacuum drying method was used to obtain the intermediate of 5'-iodo-3',4'-methylenedioxy cinnamic acid (245 mg, 70%).

5'-iodo-3',4'-methylenedioxy cinnamic acid (245 mg, 0.77 mmol), isobutenamine (71 mg, 0.97 mmol) and triethylamine (122 mg, 1.2 mmol) were dissolved in 10 ml anhydrous dichloromethane, stirred for 15 min under the condition of an ice bath and slowly added with HATU (368 mg, 0.97 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain N-isobutyl-5'-iodo-3',4'-methylenedioxy cinnamamide (200 mg, 69%).

$^1$H NMR (CDCl$_3$, 400 MHz): δ 7.45 (1H, d, J=15.6 Hz), 7.29 (1H, d, J=1.2 Hz), 6.92 (1H, d, J=1.2 Hz), 6.23 (1H, d, J=15.2 Hz), 6.05 (2H, s), 5.63 (1H, br), 3.21 (2H, t, J=6.8 Hz), 1.84 (1H, m), 0.96 (3H, s), 0.95 (3H, s);

$^{13}$C NMR (CDCl$_3$, 100 MHz): δ 165.93, 150.75, 147.20, 139.35, 131.53, 131.49, 120.47, 106.46, 106.85, 101.29, 70.86, 47.35, 28.86, 20.39;

ESI-MS: 374.0 [M+H]$^+$

Example 4 N-isobutyl-5'-chloro-3',4'-methylenedioxy cinnamamide (I-4)

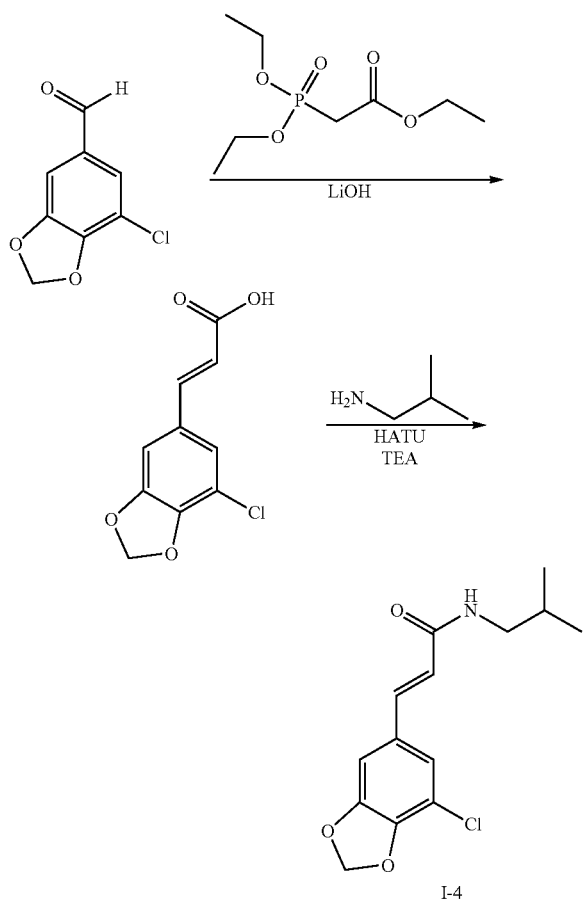

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen. 3,4-methylenedioxy-5-chlorobenzaldehyde (200 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a light-yellow solid to be precipitated. The solid was collected through filtration under reduced pressure, and then a vacuum drying method was used to obtain the intermediate of 5'-chloro-3',4'-methylenedioxy cinnamic acid (175 mg, 70%).

5'-chloro-3',4'-methylenedioxy cinnamic acid (175 mg, 0.77 mmol), isobutenamine (71 mg, 0.97 mmol) and triethylamine (122 mg, 1.2 mmol) were dissolved in 10 ml anhydrous dichloromethane, stirred for 15 min under the condition of an ice bath, and slowly added with HATU (368 mg, 0.97 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain N-isobutyl-5'-chloro-3',4'-methylenedioxy cinnamamide (160 mg, 74%).

$^1$H NMR (CDCl$_3$, 400 MHz): δ 7.40 (1H, d, J=15.6 Hz), 6.92 (1H, d, J=1.2 Hz), 6.81 (1H, d, J=1.2 Hz), 6.18 (1H, d, J=15.6 Hz), 6.00 (2H, s), 5.62 (1H, br), 3.15 (2H, t, J=6.8 Hz), 1.77 (1H, m), 0.89 (3H, s), 0.88 (3H, s);

$^{13}$C NMR (CDCl$_3$, 100 MHz): δ 165.87, 149.23, 145.59, 139.62, 130.52, 123.68, 120.60, 114.43, 105.57, 102.41, 47.34, 28.85, 20.37;

ESI-MS: 282.1 [M+H]$^+$

Example 5 N-isobutyl-5'-trifluoromethyl-3',4'-methylenedioxy cinnamamide (I-5)

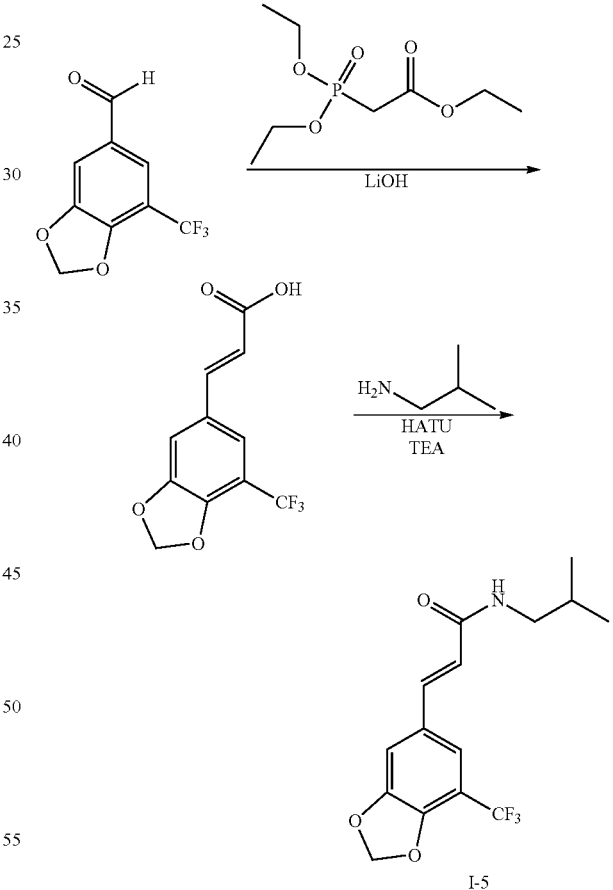

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen. 3,4-methylenedioxy-5-trifluoromethylbenzaldehyde (240 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a light-yellow solid to be precipitated. The solid was collected through filtration under reduced pressure, and then a vacuum drying method was used to obtain the intermediate of 5'-trifluoromethyl-3',4'-methylenedioxy cinnamic acid (170 mg, 59%).

5'-trifluoromethyl-3',4'-methylenedioxy cinnamic acid (170 mg, 0.65 mmol), isobutenamine (57 mg, 0.78 mmol) and triethylamine (100 mg, 0.97 mmol) were dissolved in 10 ml anhydrous dichloromethane, stirred for 15 min under the condition of an ice bath, and slowly added with HATU (300 mg, 0.78 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain N-isobutyl-5'-trifluoromethyl-3',4'-methylenedioxy cinnamamide (140 mg, 70%).

$^1$H NMR (CDCl$_3$, 400 MHz): δ 7.53 (1H, d, J=15.6 Hz), 7.17 (1H, d, J=1.2 Hz), 7.11 (1H, d, J=1.2 Hz), 6.29 (1H, d, J=15.6 Hz), 6.13 (2H, s), 5.65 (1H, br), 3.22 (2H, t, J=6.8 Hz), 1.84 (1H, m), 0.97 (3H, s), 0.95 (3H, s);

$^{13}$C NMR (CDCl$_3$, 100 MHz): δ 165.97, 149.60, 146.31, 139.08, 129.81, 123.80, 121.63, 121.29, 119.36, 109.49, 103.09, 47.42, 28.84, 20.35;

ESI-MS: 316.1 [M+H]$^+$

Example 6 N-isobutyl-5-(5'-methoxy-3',4'-methylenedioxy phenyl)pentadienamide (I-6)

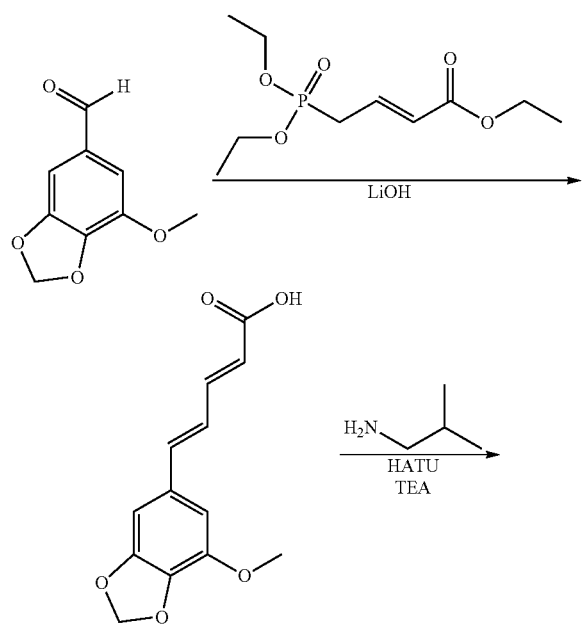

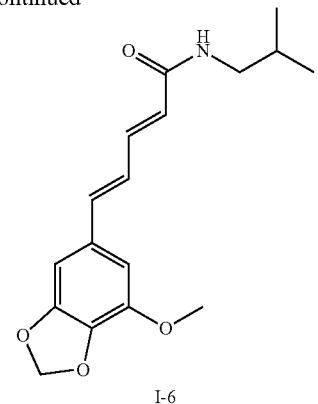

I-6

Triethyl 4-phosphonocrotonate (325 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen.

3,4-methylenedioxy-5-methoxybenzaldehyde (200 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a light-yellow solid to be precipitated. The solid was collected through filtration under reduced pressure, and then a vacuum drying method was used to obtain the intermediate of 5-(5'-methoxy-3',4'-methylenedioxy phenyl)pentadienoic acid (125 mg, 65%).

5-(5'-methoxy-3',4'-methylenedioxy phenyl)pentadienoic acid (125 mg, 0.65 mmol), isobutenamine (57 mg, 0.78 mmol) and triethylamine (100 mg, 0.97 mmol) were dissolved in 10 ml anhydrous dichloromethane, stirred for 15 min under the condition of an ice bath, and slowly added with HATU (300 mg, 0.78 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N-isobutyl-5-(5'-methoxy-3',4'-methylenedioxy phenyl)pentadienamide (140 mg, 71%).

$^1$H NMR (CDCl$_3$, 400 MHz): δ 7.29 (1H, dd, J$_1$=10.0 Hz, J$_2$=12.8 Hz), 6.69-6.58 (3H, m), 6.51 (1H, s), 5.91 (2H, s), 5.87 (1H, d, J=14.8 Hz), 5.55 (1H, br), 3.85 (3H, S), 3.12 (2H, t, J=6.4 Hz), 1.76 (1H, m), 0.88 (3H, s), 0.86 (3H, s);

$^{13}$C NMR (CDCl$_3$, 100 MHz): δ 166.45, 149.46, 143.82, 140.94, 138.97, 136.15, 131.52, 125.42, 123.83, 108.08, 101.94, 100.28, 56.78, 47.26, 28.87, 20.40;

ESI-MS: 304.2 [M+H]$^+$

Example 7 N-isobutyl-3',4'-methylenedioxy cinnamamide (I-7)

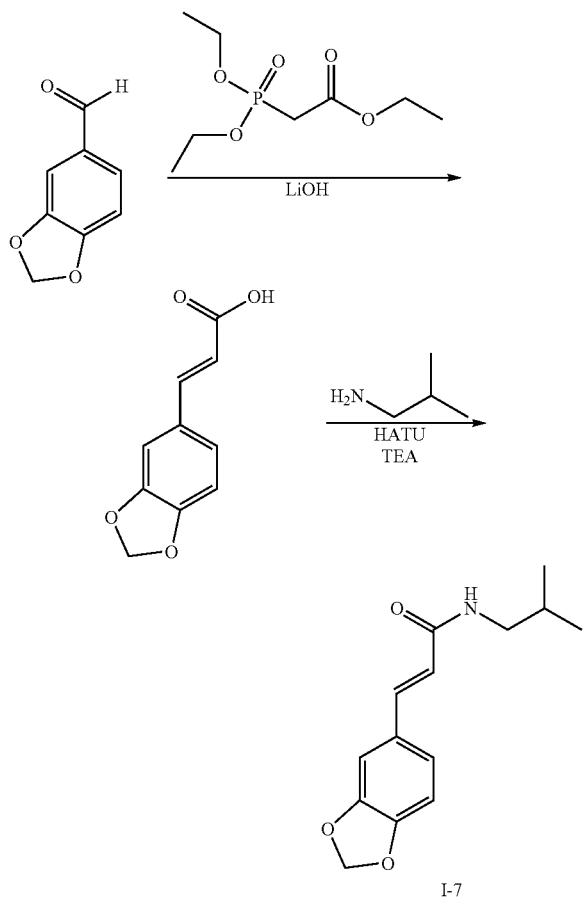

Triethyl phosphonoacetate (300 mg, 1.3 mmol), anhydrous tetrahydrofuran (10 ml) and lithium hydroxide (163 mg, 3.9 mmol) were added into a 50 ml three-necked flask, and heated to 70° C. to react for 1 hour under a protection of nitrogen. 3,4-(methylenedioxy)benzaldehyde (165 mg, 1.1 mmol) was dissolved into 5 ml anhydrous tetrahydrofuran, and the obtained solution was dripped into the flask within 0.5 hours. The reaction solution was allowed to react at 70° C. for 10 hours. Thin layer chromatography (TLC) was used to monitor the reaction. Heating was not stopped until the reaction was completed. The resultant reaction solution was concentrated to a dry solid by rotary evaporation. 20 ml distilled water was added to dissolve the solid to form a solution. 2N hydrochloride was slowly dripped into afore-said solution to adjust pH to 2.0 and stirred continuously for 1 hour to allow a light-yellow solid to be precipitated. The solid was collected through filtration under reduced pressure, and then a vacuum drying method was used to obtain the intermediate of 3',4'-methylenedioxy cinnamic acid (180 mg, 80%).

3',4'-methylenedioxy cinnamic acid (180 mg, 0.94 mmol), isobutenamine (83 mg, 1.12 mmol) and triethylamine (142 mg, 1.4 mmol) were dissolved in 10 ml anhydrous dichloromethane, stirred for 15 min under the condition of an ice bath, and slowly added with HATU (425 mg, 1.12 mmol). The resultant solution was continued to be stirred under the condition of an ice bath for 2 hours. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N-isobutyl-3',4'-methylenedioxy cinnamamide (188 mg, 81%).

$^1$H NMR (CDCl$_3$, 400 MHz): δ 7.45 (1H, d, J=20.4 Hz), 6.90 (1H, s), 6.88 (1H, d, J=10.8 Hz), 6.68 (1H, d, J=10.8 Hz), 6.22 (1H, d, J=20.8 Hz), 5.96 (1H, br), 5.89 (2H, s), 3.13 (2H, t, J=8.8 Hz), 1.77 (1H, m), 0.88 (3H, s), 0.86 (3H, s);

$^{13}$C NMR (CDCl$_3$, 100 MHz): δ 166.53, 149.10, 148.36, 140.58, 129.57, 123.92, 119.36, 108.65, 106.54, 101.59, 47.35, 28.87, 20.35;

ESI-MS: 248.1 [M+H]$^+$

Example 8 N,N-dimethyl-5'-trifluoromethyl-3',4'-methylenedioxy cinnamamide (I-8)

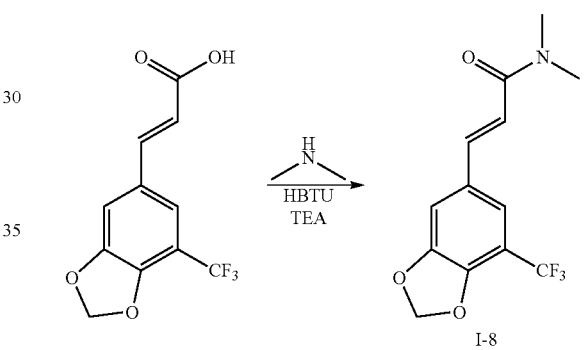

5'-trifluoromethyl-3',4'-methylenedioxy cinnamic acid (200 mg, 0.77 mmol), dimethyl amine (1.54 mmol) in anhydrous tetrahydrofuran, and triethylamine (233 mg, 2.3 mmol) were dissolved into 20 ml anhydrous dichloromethane and stirred under the condition of an ice bath for 15 min. The obtained solution was slowly added with HBTU (352 mg, 0.92 mmol) and stirred for 2 hours under the condition of an ice bath. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N,N-dimethyl-5'-trifluoromethyl-3',4'-methylenedioxy cinnamamide (200 mg, 90%).

$^1$H NMR (CDCl$_3$, 400 MHz): δ 7.57 (1H, d, J=15.6 Hz), 7.18 (1H, s), 7.15 (1H, s), 6.78 (1H, d, J=15.6 Hz), 6.14 (2H, s), 3.19 (3H, s), 3.08 (3H, s);

$^{13}$C NMR (CDCl$_3$, 100 MHz): δ 166.24, 149.44, 146.15, 140.62, 130.01, 123.89, 121.19, 119.26, 117.28, 109.40, 102.91, 37.43, 35.98;

$^{19}$F NMR (CDCl$_3$, 400 MHz): δ −61.48

ESI-MS: 310.1 [M+Na]$^+$

Example 9 N,N-diethyl-5'-trifluoromethyl-3',4'-methylenedioxy cinnamamide (I-9)

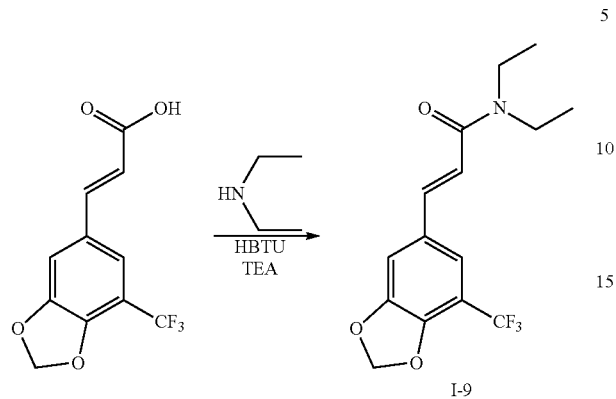

5'-trifluoromethyl-3',4'-methylenedioxy cinnamic acid (300 mg, 1.15 mmol), diethyl amine (170 mg, 2.3 mmol), and triethylamine (350 mg, 3.45 mmol) were dissolved into 10 ml anhydrous dichloromethane and stirred under the condition of an ice bath for 15 min. The obtained solution was slowly added with HBTU (530 mg, 1.38 mmol) and stirred for 2 hours under the condition of an ice bath. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain N,N-diethyl-5'-trifluoromethyl-3',4'-methylenedioxy cinnamamide (350 mg, 96%).

$^1$H NMR (CDCl$_3$, 400 MHz): δ 7.61 (1H, d, J=15.2 Hz), 7.17 (1H, s), 7.16 (1H, s), 6.71 (1H, d, J=15.2 Hz), 6.14 (2H, s), 3.53-3.46 (4H, m), 1.28 (3H, t, J=7.2 Hz), 1.20 (3H, t, J=7.2 Hz);

$^{13}$C NMR (CDCl$_3$, 100 MHz): δ 165.23, 149.42, 146.08, 140.59, 130.16, 123.91, 121.20, 119.22, 117.66, 109.36, 102.89, 42.30, 41.13, 15.13, 13.19;

$^{19}$F NMR (CDCl$_3$, 400 MHz): δ −61.48

ESI-MS: 338.1 [M+Na]$^+$

Example 10 1-(5'-trifluoromethyl-3',4'-methylenedioxy cinnamyl)-piperidine (I-10)

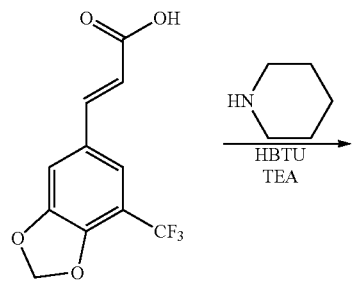

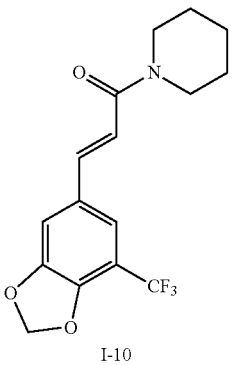

5'-trifluoromethyl-3',4'-methylenedioxy cinnamic acid (300 mg, 1.15 mmol), piperidine (195 mg, 2.3 mmol), and triethylamine (350 mg, 3.45 mmol) were dissolved into 10 ml anhydrous dichloromethane and stirred under the condition of an ice bath for 15 min. The obtained solution was slowly added with HBTU (530 mg, 1.38 mmol) and stirred for 2 hours under the condition of an ice bath. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain 1-(5'-trifluoromethyl-3',4'-methylenedioxy cinnamyl)-piperidine (350 mg, 92%).

$^1$H NMR (CDCl$_3$, 400 MHz): δ 7.55 (1H, d, J=15.6 Hz), 7.18 (1H, s), 7.15 (1H, s), 6.80 (1H, d, J=15.6 Hz), 6.14 (2H, s), 3.63 (4H, br), 1.72-1.68 (2H, m), 1.64-1.60 (4H, m);

$^{13}$C NMR (CDCl$_3$, 100 MHz): δ 164.86, 149.43, 146.06, 140.47, 130.19, 123.93, 121.23, 119.06, 117.64, 109.43, 102.89, 47.07, 43.44, 26.77, 25.68, 24.64;

$^{19}$F NMR (CDCl$_3$, 400 MHz): δ −61.46

ESI-MS: 350.1 [M+Na]$^+$

Example 11 N-isobutyl-3-(5'-trifluoromethyl-3',4'-methylenedioxy phenyl)-propionamide (I-11)

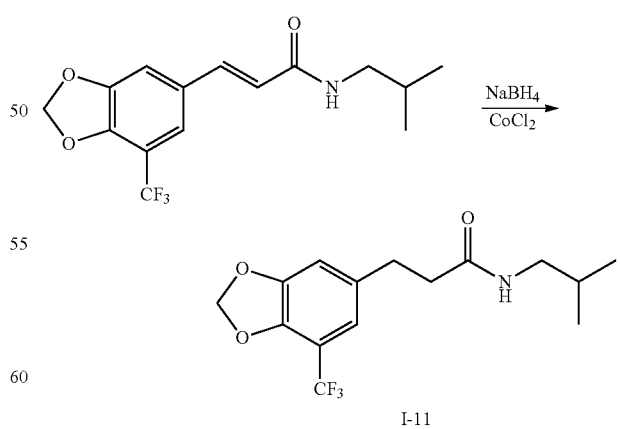

N-isobutyl-5'-trifluoromethyl-3',4'-methylenedioxy cinnamamide (200 mg, 0.63 mmol) were dissolved into 30 ml methanol and added with CoCl$_2$.6H$_2$O (600 mg, 2.54 mmol) under the condition of an ice bath. After 0.5 hours of agitation, NaBH$_4$ (195 mg, 5.1 mmol) was batch-added into the obtained solution, heated to room temperature one hour later, and continued to stir for 2 hours. After stopping agitation, the solvent was evaporated to dry. The crude product was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=5/1) to obtain N-isobutyl-3-(5'-trifluoromethyl-3',4'-methylenedioxy phenyl)-propionamide (140 mg, 70%).

$^1$H NMR (CDCl$_3$, 400 MHz): δ 6.86 (1H, s), 6.85 (1H, s), 6.06 (2H, s), 5.55 (1H, br), 3.06 (2H, t, J=6.4 Hz), 2.93 (2H, t, J=7.2 Hz), 2.45 (2H, t, J=7.2 Hz), 1.75-1.68 (1H, m), 0.87 (3H, s), 0.85 (3H, s);

$^{13}$C NMR (CDCl$_3$, 100 MHz): δ 171.44, 148.91, 143.54, 135.21, 124.21, 121.51, 117.42, 112.01, 102.29, 46.89, 38.39, 31.27, 28.44, 19.98;

$^{19}$F NMR (CDCl$_3$, 400 MHz): δ -119.72;

ESI-MS: 340.1 [M+Na]$^+$

Example 12
N-isobutyl-5-trifluoromethyl-3,4-methylenedioxy benzamide (I-12)

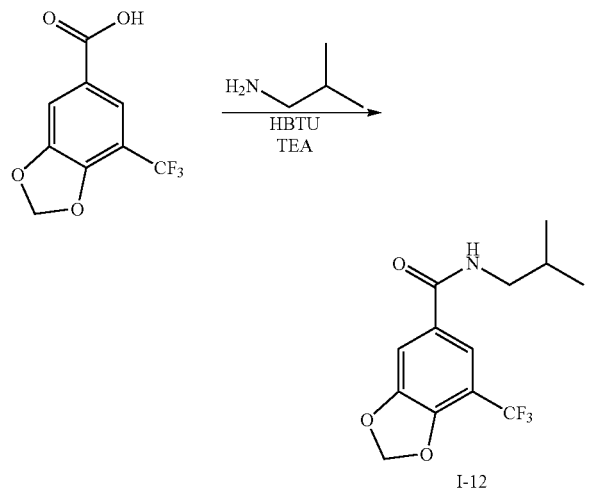

5-trifluoromethyl-3,4-methylenedioxy benzoic acid (260 mg, 1.11 mmol), isobutyl amine (162 mg, 2.22 mmol) and triethylamine (330 mg, 3.33 mmol) were dissolved into 10 ml anhydrous dichloromethane and stirred under the condition of an ice bath for 15 min. The obtained solution was slowly added with HBTU (500 mg, 1.33 mmol) and stirred for 2 hours under the condition of an ice bath. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain N-isobutyl-5-trifluoromethyl-3,4-methylenedioxy benzamide (250 mg, 78%).

$^1$H NMR (CDCl$_3$, 400 MHz): δ 7.46 (1H, s), 7.41 (1H, s), 6.37 (1H, br), 6.16 (2H, s), 3.26 (2H, t, J=6.4 Hz), 1.95-1.85 (1H, m), 0.98 (3H, s), 0.96 (3H, s);

$^{13}$C NMR (CDCl$_3$, 100 MHz): δ 165.73, 149.27, 147.56, 129.47, 123.79, 121.08, 117.73, 110.40, 103.19, 47.57, 28.59, 20.16;

$^{19}$F NMR (CDCl$_3$, 400 MHz): δ -61.45;

ESI-MS: 312.1 [M+Na]$^+$

Example 13
1-(5-trifluoromethyl-3,4-methylenedioxy benzoyl)-piperidine (I-13)

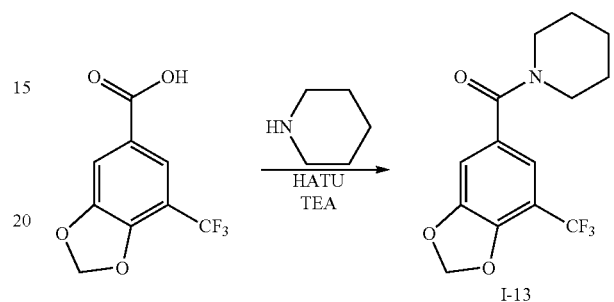

5-trifluoromethyl-3,4-methylenedioxy benzoic acid (260 mg, 1.11 mmol), piperidine (190 mg, 2.22 mmol) and triethylamine (330 mg, 3.33 mmol) were dissolved into 10 ml anhydrous dichloromethane and stirred under the condition of an ice bath for 15 min. The obtained solution was slowly added with HBTU (500 mg, 1.33 mmol) and stirred for 2 hours under the condition of an ice bath. After stopping agitation, 20 ml water was added and shaken to separate the organic phase. The aqueous phase was extracted with dichloromethane (2×20 ml). After combining the organic phases, anhydrous sodium sulfate was used to dry, and the resultant solution was concentrated under reduced pressure to dryness. The raw product was purified by silica gel column chromatography (eluent: petroleum ether/ethyl acetate=3/1) to obtain 1-(5-trifluoromethyl-3,4-methylenedioxy benzoyl)-piperidine (280 mg, 87%).

$^1$H NMR (CDCl$_3$, 400 MHz): δ 7.11 (1H, s), 7.03 (1H, s), 6.14 (2H, s), 3.64-3.41 (4H, m), 1.69-1.62 (6H, m);

$^{13}$C NMR (CDCl$_3$, 100 MHz): δ 168.37, 148.91, 146.11, 130.45, 123.82, 121.12, 117.72, 110.69, 102.91, 102.91, 29.73, 24.53;

$^{19}$F NMR (CDCl$_3$, 400 MHz): δ -61.48;

ESI-MS: 324.1 [M+Na]$^+$

Example 14 Preparation of Tablets of N-isobutyl-5'-trifluoromethyl-3',4'-methylenedioxy cinnamamide N-isobutyl-5'-trifluoromethyl-3',4'-methylenedioxy cinnamamide (I-5) was taken, mixed with starch, dextrin, microcrystalline cellulose and magnesium stearate in accordance with a conventional method to prepare into wet granules. Tablets were prepared by machine punching, and a coating step was performed to obtain coated tablets. Each tablet contained 20 mg of N-isobutyl-5'-trifluoromethyl-3',4'-methylenedioxy cinnamamide. Usage: twice per day and 1~2 tablets per time.

Example 15 Preparation of Capsules of N-isobutyl-5'-trifluoromethyl-3',4'-methylenedioxy cinnamamide N-isobutyl-5'-trifluoromethyl-3',4'-methylenedioxy cinnamamide (I-5), lactose and hydroxypropyl cellulose (HPC)

screened by using a 60 mesh sieve were mixed well, added with an appropriate amount of Tween-80 and then added 3% aqueous hydroxypropyl methylcellulose (HMPC) solution, and passed through a 20 mesh sieve. The obtained granules were subjected to air drying in baking oven. Dried material was added with talc powder, mixed well and loaded into capsule shell. Each capsule contained 20 mg of N-isobutyl-5'-trifluoromethyl-3',4'-methylenedioxy cinnamamide. Usage: twice per day and 1~2 capsules per time.

Said applications of the present invention in the field of pharmaceutics are not completely limited to those disclosed herein in any way. Said raw medicine is any one of compounds or their pharmaceutically acceptable acid addition salts descried in the present invention.

Said dosage forms are not completely limited to those disclosed herein in any way. Said compounds can be prepared into more other pharmaceutically acceptable dosage forms, e.g. drop pills, sustainable released formulations etc.

What is claimed is:

1. A compound of a general formula (I) or its pharmaceutically acceptable acid addition salts:

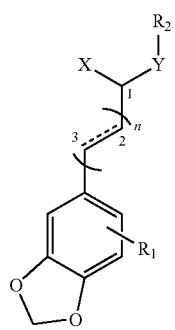

(I)

wherein:
(i) $R_1$ is F, Cl, Br, I, $OCF_3$, $OCHF_2$, $OCH_2F$, $CF_3$, $CHF_2$, $CH_2F$, $CH_3$, $CH_3CH_2$, $CF_3CH_2$, $NO_2$,
n represents 0 or 1, and the unit of

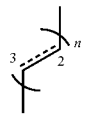

represents carbon-carbon single or double bond;
X is =O;
Y is $NR_3$, wherein said $R_3$ is H, $C_1$~$C_{10}$ straight chain hydrocarbyl; $C_3$~$C_{10}$ branched chain hydrocarbyl, and
$R_2$ is H, $C_1$~$C_{10}$ straight chain hydrocarbyl, $C_3$~$C_{10}$ branched chain hydrocarbyl group; or
Y is N and $R_2$ is a group which forms piperidyl group with the neighboring Y; or
(ii) $R_1$ is F, Cl, Br, I, $OCH_3$, $OCF_3$, $OCHF_2$, $OCH_2F$, $CF_3$, $CHF_2$, $CH_2F$, $CH_3$, $CH_3CH_2$, $CF_3CH_2$, $NO_2$;
n represents 2, and the unit of

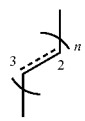

represents carbon-carbon single or double bond;
X is =O;
Y is $NR_3$, wherein said $R_3$ is H, $C_1$~$C_{10}$ straight chain hydrocarbyl; $C_3$~$C_{10}$ branched chain hydrocarbyl;
$R_2$ is H, $C_1$~$C_{10}$ straight chain hydrocarbyl, $C_3$~$C_{10}$ branched chain hydrocarbyl group.

2. The compound or its pharmaceutically acceptable acid addition salts according to claim 1, wherein
(i) $R_1$ is —$CF_3$;
n represents 0 or 1, and

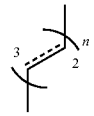

represents carbon-carbon single or double bond;
X is =O;
Y is NH and
$R_2$ is H, $C_1$~$C_{10}$ straight chain hydrocarbyl, $C_3$~$C_{10}$ branched chain hydrocarbyl group; or
Y is N and $R_2$ is a group which forms piperidyl group with the neighboring Y; or
(ii) $R_1$ is $CF_1$;
n represents 2, and

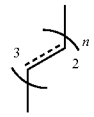

represents carbon-carbon single or double bond;
X is =O;
Y is NH, and $R_2$ is H, $C_1$~$C_{10}$ straight chain hydrocarbyl, $C_3$~$C_{10}$ branched chain hydrocarbyl group.

3. The compound or its pharmaceutically acceptable acid addition salts according to claim 1, wherein the substituted cinnamamide derivatives of a general formula (II)

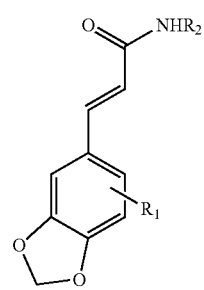

(II)

wherein, $R_1$ is F, Cl, Br, I, $OCF_3$, $OCHF_2$, $OCH_2F$, $CF_3$, $CHF_2$, $CH_2F$, $CH_3$, $CH_3CH_2$, $CF_3CH_2$, $NO_2$;
$R_2$ is H, $C_1$~$C_{10}$ straight chain hydrocarbyl, $C_3$~$C_{10}$ branched chain hydrocarbyl group.

4. A compound or its pharmaceutically acceptable acid addition salts, wherein the compound is selected from the group consisting of:
N-isobutyl-5'-nitro-3',4'-methylenedioxy cinnamamide;
N-isobutyl-5'-iodo-3',4'-methylenedioxy cinnamamide;
N-isobutyl-5'-chloro-3',4'-methylenedioxy cinnamamide;

N-isobutyl-5'-trifluoromethyl-3',4'-methylenedioxy cinnamamide;

N-isobutyl-5-(5'-methoxy-3',4'-methylenedioxy phenyl) pentadienamide;

N,N-dimethyl-5'-trifluoromethyl-3',4'-methylenedioxy cinnamamide;

N,N-diethyl-5'-trifluoromethyl-3',4'-methylenedioxy cinnamamide;

1-(5'-trifluoromethyl-3',4'-methylenedioxy cinnamyl)-piperidine;

N-isobutyl-3-(5'-trifluoromethyl-3',4'-methylenedioxy phenyl)-propionamide;

N-isobutyl-5-trifluoromethyl-3,4-methylenedioxy benzamide; and 1-(5-trifluoromethyl-3,4-methylenedioxy benzoyl)-piperidine.

5. The compound or its pharmaceutically acceptable acid addition salts according to claim 1, wherein said acceptable acid addition salts are prepared by reacting the compound of the general formula (I) with the following acids: sulfuric acid, hydrochloric acid, hydrobromic acid, phosphoric acid, tartaric acid, fumaric acid, maleic acid, citric acid, acetic acid, formic acid, methane sulfonic acid, p-toluene sulphonic acid, oxalic acid or succinic acid.

6. A pharmaceutical composition containing the compound of claim 1 or its pharmaceutically acceptable acid addition salts.

7. The pharmaceutical composition according to claim 6, wherein said composition further contains pharmaceutically acceptable carrier(s).

8. A method for preparing the compound or its pharmaceutically acceptable acid addition salts according to claim 1, comprising the following steps:
  a. reacting a substituted piperonal derivative with ethoxyformyl methylene triphenyl phosphine or triethyl phosphonoacetate by a Wittig reaction or Wittig-Horner reaction to obtain a substituted cinnamic acid derivative;
  b. obtaining an acylated derivative (including acyl halide, azide, anhydride, active ester) of the substituted cinnamic acid derivative from the substituted cinnamic acid derivative, and reacting the acylated derivative with an organic amine to obtain an amide derivative;

Alternatively, reacting the substituted cinnamic acid derivative with an organic amine and a condensing agent (HATU, HBTU, EDCI, DCC etc.) to obtain an amide derivative;

or using 5'-trifluoromethyl-3',4'-methylenedioxy cinnamic acid as a starting material to obtain an acylated derivative (including acyl halide, azide, anhydride, active ester) thereof, and reacting the acylated derivative with an organic amine to obtain an amide derivative; or reacting 5'-trifluoromethyl-3',4'-methylenedioxy cinnamic acid with an organic amine and a condensing agent (HATU, HBTU, EDCI, DCC etc.) to obtain an amide derivative;

preparing a derivative containing carbon-carbon single bond in its side chain by reducing a derivative containing carbon-carbon double bond in its side chain with a catalytic hydrogenation or sodium borohydride.

9. A method of treating a depressive-type mental disease comprising the administration to an individual in need thereof a pharmaceutical composition comprising a compound of formula (I) as in claim 1.

10. The method according to claim 9, wherein said compound is selected from the group consisting of:

N-isobutyl-5'-nitro-3',4'-methylenedioxy cinnamamide;
N-isobutyl-5'-iodo-3',4'-methylenedioxy cinnamamide;
N-isobutyl-5'-chloro-3',4'-methylenedioxy cinnamamide;
N-isobutyl-5'-trifluoromethyl-3',4'-methylenedioxy cinnamamide;
N-isobutyl-5-(5'-methoxy-3',4'-methylenedioxy phenyl) pentadienamide;
N,N-dimethyl-5'-trifluoromethyl-3',4'-methylenedioxy cinnamamide;
N,N-diethyl-5'-trifluoromethyl-3',4'-methylenedioxy cinnamamide;
1-(5'-trifluoromethyl-3',4'-methylenedioxy cinnamyl)-piperidine;
N-isobutyl-3-(5'-trifluoromethyl-3',4'-methylenedioxy phenyl)-propionamide;
N-isobutyl-5-trifluoromethyl-3,4-methylenedioxy benzamide; and
1-(5-trifluoromethyl-3,4-methylenedioxy benzoyl)-piperidine.

* * * * *

UNITED STATES PATENT AND TRADEMARK OFFICE
CERTIFICATE OF CORRECTION

PATENT NO. : 10,071,989 B2
APPLICATION NO. : 14/128572
DATED : September 11, 2018
INVENTOR(S) : Xiaohu Ma et al.

Page 1 of 1

It is certified that error appears in the above-identified patent and that said Letters Patent is hereby corrected as shown below:

In the Claims

In Claim 2, Column 34, Line 26, the "$CF_1$" should read --$CF_3$--.

Signed and Sealed this
Sixth Day of November, 2018

Andrei Iancu
*Director of the United States Patent and Trademark Office*